(12) United States Patent
Tanksley et al.

(10) Patent No.: US 6,664,447 B2
(45) Date of Patent: Dec. 16, 2003

(54) TOMATO GENE.SW-5 CONFERRING RESISTANCE TO TOSPOVIRUSES

(75) Inventors: Steven D. Tanksley, Ithaca, NY (US); Sergio H. Brommonschenkel, Viçosa-MG (BR)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/803,286

(22) Filed: Mar. 9, 2001

(65) Prior Publication Data

US 2002/0062504 A1 May 23, 2002

Related U.S. Application Data

(60) Provisional application No. 60/188,356, filed on Mar. 10, 2000.

(51) Int. Cl.$^7$ .......................... C12N 15/29; C12N 15/82; C12N 15/90; A01H 5/00; A01H 5/10
(52) U.S. Cl. .................... 800/301; 435/320.1; 435/419; 435/468; 435/471; 536/23.6; 800/279; 800/298; 800/317.4
(58) Field of Search .............................. 435/320.1, 410, 435/411, 419, 468, 471; 536/23.6; 800/278, 279, 280, 295, 298, 301, 317.4

(56) References Cited

U.S. PATENT DOCUMENTS

| | | | |
|---|---|---|---|
| 5,750,386 A | 5/1998 | Conkling et al. | 435/468 |
| 5,907,084 A | 5/1999 | de Haan | 800/279 |
| 5,919,705 A | 7/1999 | de Haan | 435/418 |
| 5,968,828 A | 10/1999 | Pehu et al. | 435/418 |

OTHER PUBLICATIONS

Jahn et al, "Genetic Mapping of the Tsw Locus for Resistance to the Tospovirus . . . Gene for Resistance to the Same Pathogen in Tomato", 2000, MPMI vol. 13, No. 6, pp. 673–682.*

Haan et al, "Characterization of RNA–Mediated Resistance to Tomato spotted wilt virus in transgenic tobacco plants", Oct. 1992, Biotechnology vol. 10, pp. 1133–1137.*

Brommonschenkel et al, "The broad–spectrum tospovirus resistance gene Sw–5 of tomato is a homolog of the root–knot nematode resistance gene Mi", 2000, MPMI vol. 13 No. 10, pp. 1130–1138.*

McCormick et al, "Leaf disc transformation of cultivated tomato (*L. esculentum*) using *Agrobacterium tumefaciens*", 1986, Plant Cell Reports vol. 5, pp. 81–84.*

Kovalenko et al., "Production of Fertile Somaclones of Interspecific Tobacco Hybrids Having a High Resistance to Tomato Spotted Wilt Virus," *Cytology and Genetics* 23(4):64–68 (1989).

Pang et al., "Resistance to Heterologous Isolates of Tomato Spotted Wilt Virus in Transgenic Tobacco Expressing Its Nucleocapsid Protein Gene," *Phytopathology* 82(10):1223–1229 (1992).

Pang et al., "The Biological Properties of a District Tospovirus and Sequence Analysis of Its S RNA," *Phytopathology* 83(7):728–733 (1993).

Prins et al., "Broad Resistance to Tospoviruses in Transgenic Tobacco Plants Expressing Three Tospoviral Nucleoprotein Gene Sequences," *Molecular Plant–Microbe Interactions* 8(1):85–91 (1995).

Chagué et al., "Identification and Mapping on Chromosome 9 of RAPD Markers Linked to *Sw–5* in Tomato by Bulked Segregant Analysis," *Theoretical and Applied Genetics* 92(8):1045–1051 (1996).

Brommonschenkel et al., "Map–Based Cloning of the Tomato Genomic Region that Spans the *Sw–5* Tospovirus Resistance Gene in Tomato," *Molecular and General Genetics* 256(2):121–126 (1997).

Folkertsma et al., "Construction of a Bacterial Artificial Chromosome (BAC) Library of *Lycopersicon esculentum* cv. Stevens and its Application to Physically Map the *Sw–5* Locus," *Molecular Breeding* 5(2):197–207 (1999).

* cited by examiner

*Primary Examiner*—Ashwin Mehta
(74) *Attorney, Agent, or Firm*—Nixon Peabody LLP

(57) ABSTRACT

The present invention relates to an isolated plant nucleic acid which confers resistance to Tospoviruses as well as expression systems, host cells, and transgenic plants transformed with such a nucleic acid. Other aspects of the present invention relate to a method of imparting to plants, resistance to Tospoviruses by transforming plants with the nucleic acid of the present invention or to a method of eliciting a hypersensitive response in plants.

24 Claims, 9 Drawing Sheets

FIG. 4C

```
   1 MAENEIEEML EHLRRIKSGG DLDWLDILRI EELEMVLRVF RTFTKYHDVL LPDSLVELTK
  61 RAKLTGEILH RVLGRIPHKC KTNLNLERLE SHLLEFFQGN TASLSHNYEL NDFDLSKYMD
 121 CLENFLNDVL MMFLQKDRFF HSREQLAKHR SIKELKIVQK KIRFLKYIYA TEINGYVDYE
 181 KQECLENRIQ FMTNTVGQYC LAVLDYVTEG KLNEENDNFS KPPYLLSLIV LVELEMKKIF
 241 HGEVKASKFT QSKTFKDKKL PKGFSHHLHN LLMYLRNKKL ENFPNNIAAQ NIDVAIEFLL
 301 VFLDADVSNH VINGNWLKKV LLKVGAIAGD ILYVIQKLLP RSINKDETSN ISLCSIQILE
 361 KTKDLKAQVE TYYKSLKFTP SQFPTFGGLS FLNSLLRKLN EMSTSKSGLG FLMKPLLGNL
 421 EKELSSLTSI LEKELSSIFR DVVHHEHNIP KDLQRRTINL SYEAEVAIDS ILAQYNAFLH
 481 IFCSLPTIVK EIKQINAEVT EMWSADIPLN PHYVAAPLKH LPDRHSNLVT DEEVVGFENK
 541 AEELIDYLIR GTNELDVVPI VGMGGGGKTT IARKLYNNDI IVSRFDVRAW CIISQTYNRR
 601 ELLQDIFSQV TGSDDNGATV DVLADMLRRK LMGKRYLIVL DDMWDCMVWD DLRLSFPDDG
 661 IRSRIVVTTR LEEVGKQVKY HTDPYSLPFL TTEESCQLLQ KKVFQKEDCP PELQDVSQAV
 721 AEKCKGLPLV VVLVAGIIKK RKMEESWWNE VKDALFDYLD SEFEEYSLAT MQLSFDNLPH
 781 CLKPCLLYMG MFSEDARIPA STLISLWIAE GFVENTESGR LMEEEAEGYL MDLISSNLVM
 841 LSKRTYKGRV KYCQVHDVVH HFCLEKSREA KFMLAVKGQY IHFQPSDWKG TRVSFSFSEE
 901 LSKFASLVSK TQKPFHQHLR SLITTNRAKS INDIFSCQIS ELRLLKVLDL SSYIVEFLSL
 961 ATFKPLNQLK YLAVQAFEFY FDPGSHLPHI ETFIVMNLPY YDILLPVSFW EMKKLRHAHF
1021 GKAEFDKQGL SEGGSSKLENL RILKNIVGFD RVDVLSRRCP NLQQLQITYF GNNEEPFCPK
1081 LENLTQLQQL QLSFARPRTL SGLQLPSNLN KLVLEGIHIE SVIPFIAGLP SLEYLQLQDV
1141 CFPQSEEWCL GDITFHKLKL LKLVKLNISR WDVSEESFPL LETLVIKKCI DLEEIPLSFA
1201 DIPTLEQIKL IGSWKVSLED SAVRMKEEIK DTEGCDRLHL VKQRSD
```

```
             *        20         *        40         *        60         *        80
Sw-5   : ELDVVPIVGMGGQGKTTIARKLYNNDITVSRFDVRAWCIISQTYNRRELLQDIFSQV-TGSD------DNGATVDV-LAD--
Mil.2  : DLDVISITGMPGSGKTTLAYKVYNDKSVSRHFDLRAWCTVDQGYDDKKLLDTIFSQV-SG-S------DSNLSENIDVAD--
Prf    : ELDVISIVGMPGLGKTTLAKKIYNDPEVTSRFDVHAQCVVTQLYSWRELLLTILNDV-LEPS------DRNEKEDGEIAD--
Rx     : ELEVVSIVGMGMGIGKTTLATKLYSDPCIMSRFDIRAKATVSQEYCVRNVLLGLSLT-SDEP------------QLAD----
I2C-1  : NLAVVPIVGMGIVGGMGKTIAKAVYNDERVQKHFGLTAWFCVSEAYDAFRITKGLLQEI-GSTDLKADDNLNQLQVKLKADDNLNQLQ
I2C-2  : NLTVVPIVGMGGLGKTTLAKAVVNDESVKNHFDLKAWFCVSEAYNAFRITKGLLQEI-GSIDL-------VDDNLNQLQ
RPM1   : QRIVVAVVGMGGSGKTTLSANIFKSQSVRRHFESYAWVTISKSYVIEDVFRTMIKEFYKEADTQIPAELYSLGYR-------ELV
                                              ————————
                                              KINASE-1a
             *       100         *       120         *       140         *       160
Sw-5   : -MIRRKLMGKRYLIVLDDMWD--CMVWDDLRLSFPDDGIRSRIVVTTRLEEVGKQV-KYHTDPYSLPFLTTEESCQLLQKKVFQKE
Mil.2  : -KIRKQLFGKRYLIVLIDDVWD--TTTLDEITRPFPEAKKGSRILLTTREKEVALHG-KLNTDPLDLRLLRPDESWELLDKRTFGNE
Prf    : -ELRRFLLTKRFLILDDVWD--YKVWDNLCMCFSDVSNRSRIILTTRLNDVAEYV-KCESDPHHLRLFRDDESWTLLQKEVFQGE
Rx     : -RLQKHLKGRRYLVVIDDIWT--TEAAWDDIKLCFPDCYNGSRILLFLQGDIGSKIIVTTRNVEVAEFYA-SSGKPPHHMRLMNFDESWNLLHKKIFEKE
I2C-1  : VKLKEKLNGKRFLVVLLDDVWNDNYPEWDDLRNLFVQGDIGSKIIVTTRKESVAL---MMDSGAIYMGILSSEDSWALFKRHSLEHK
I2C-2  : VKLKERLKEKKFLIVLDDVWNDNYNEWDELRNVFVQGDIGSKIIVTTRKDSVAL---MMGNEQISMGNLSTEASWSIFQRHAFENM
RPM1   : EKLVEYLQSKRYIVVLDDVWTTG--LWREISIALPDGIYGSRVMTTRDMNVASFPYGIGSTKHEJELLKEDEAWVLFSNKAFPAS
                                              ———————        ————————
                                              KINASE-2        KINASE-3a
             *       180         *       200         *       220         *       240         *
Sw-5   : -D-CPPE-LQDVSQAVAEKCKGLPLVVVLVAGIIKKRKMEESWWNEVKDALFDYLDSEFEEYSLATMQ-LSFDNLPHCLLKPCLLYM
Mil.2  : -S-CPDE-LLDVGKEIAENCKGLPLIVADLIAGVIAGREKKRSVWLEVQSSLSSFILNSEVE-VMKVIE-LSYDHLPHHLKPCLLHF
Prf    : -S-CPPE-LEDVGFEISKSCRGLPLISVVLVAGVLAGLIAGLIAGMIRSKS-EVDEWRNILRSEIWELPSCSNG--ILPALM-LSYNDLPAHLKQCFAYC
Rx     : GS-YSPE-FENIGKQIALKCGGLPLAITVIAGLIAGLAGMIRSKS-EVDEWRNILRSEIWELPSCSNG--ILPALM-LSYNDLPAHLKQCFAYC
I2C-1  : DPKEHPE-FEEVGKQIADKCKGLPLAAKCKGLPLALKTLAGMIRSKS-EVEEWKCILRSEIWELR--DND--ILPALM-LSYNDLPAHLKRCFSFC
I2C-2  : DPMGHSE-LEEVGRQIAAKCKGLPLALKTLAGMIRSKS-EVEEWKCILRSEIWELR--DND--ILPALM-LSYNDLPAHLKRCFSFC
RPM1   : LEQCRTQNLEPIARKLVERCQGLPLAIASLGSMSTKKFE-SEWKKVYSTLNWELNNNHELKIVRSIMFLSFNDLPYPLKRCFLYC
                                     ——
                                     hd
```

FIG. 5B

```
Sw-5   : HQHLRSL--ITTNRAKSINDIFSCQISELRLLKVLDLSSYIVEFLS--LATFKPLNQLKYLAVQAFEFYFDPG-SHLPHIETFIVMNL
Mi1.2  : GKHIYSLRINGDQLDDSVSDAF--HLRHLRLIRVLDIEPSLIMVNDSLLNEICMNHLRYLRIRTQVKYLPFSFSNLMWNLESLFVSNK
Prf    : VRSLFNAIDPDNLLWPRDISFI--FESFKLVKVLDLESFNIG--GTFPTEIQYLIQMKYFAAQTDANSIPSSIAKLENLETFVVRGL

Sw-5   : PYYDILPVSFWEMKKLRHAHFGKAEF-----DKQGLSEGSSKLENLRILKNI-VGFDRVDV-LSRRCPNLQQLQITY----FGNNE
Mi1.2  : GSILVLP-RILDLVKLRLRVLSVGACSFFDMDADESILIAKDTKLENLRILGELLISYSKDTMNIFKRFPNLQVLQFELKESWDYSTEQ
Prf    : GGEMIL-PCSLLKMVKLRHIHVNDRVSFGLHENMDVLTG-NSQLPNLETFSTPRLFYGKDAEKVLRKMPKLRKLSCIFSGTFGYSRKL

Sw-5   : EPFC----PKLENLTQLQLQLPFARPRTLS---------GLQLPSNLNKLVLEGIHTGC-VIPFIAGLPSLEYLQLHDVCFPQSEE
Mi1.2  : HWF----PKLDCLTELETLCVGFKSSNTNHCGSSVTNRPWDFHFPSNLKELLYDFPLTSDSLSTIARLPNLENLSLYDTII-QGEE
Prf    : KGRCVRFPRLDFLSHLESLKLV--------SNSYPAKLPHKFNFPSQLRELTLSKFRLPWTQISIIAELPNLVILKLLLRAF-EGDH

Sw-5   : WCLGDI-TFHKLKLEKLVKLNISRWDVSEESFPLLETLVIKKCIDLEEIPLSFADIPTLEQIKLIGSW-KVSLEDSAVRMKEEIKDTE
Mi1.2  : WNMGEEDTFENLKFLNLRLTLSKMEVGEESFPNLEKLKLQECGKLEEIPPSFGDIYSLKFIKIVKS---PQLEDSALKIKKYAEDMR
Prf    : WEVKDSE-FLELKYLKLDNLKVVQMSISDDAFFKLEHLVLTCKKHLEKIPSRFEDAVCLNRVEV--NWCNWNVANSAQDIQTMQHEVI

Sw-5   : GCDRLHLIVKQ------RS----D
Mi1.2  : GGNDLQILGQ------KNIPLFK
Prf    : ANDSFTVTIQPPDWSKEQPLDS
```

FIG. 5C

TOMATO GENE.SW-5 CONFERRING RESISTANCE TO TOSPOVIRUSES

This application claims benefit of U.S. Provisional Patent Application Serial No. 60/188,356, filed Mar. 10, 2000.

This invention was developed with government funding under the National Research Initiative Cooperative Grants Program, U.S. Department of Agriculture Plant Genome Program No. 97-35301-4422. The U.S. Government may have certain rights.

FIELD OF THE INVENTION

The present invention relates to a plant nucleic acid which confers resistance to plants to Tospoviruses, and uses thereof.

BACKGROUND OF THE INVENTION

Tospoviruses are thrips-transmitted viruses that belong to the genus Tospovirus (family Bunyaviridae) and cause substantial yield loss to ornamental and vegetable crops in several areas of the world (German et al., "Tospoviruses: Diagnosis, Molecular Biology, Phylogeny, and Vector Relationships," *Annu. Rev. of Phytopathol* 30:315–348 (1992); Peters et al., "Vector Relations in the Transmission and Epidemiology of Tospoviruses. In: International Symposium on Tospoviruses and Thrips of Floral and Vegetable Crops," *Acta Horticulturae* 431:29–42 (1996)). The members of this genus are characterized by a genome comprised of three separate single stranded RNAs (S, M, and L RNAs) enveloped in a lipidic membrane and associated with two glycoproteins, G1 and G2 (German et al., "Tospoviruses: Diagnosis, Molecular Biology, Phylogeny, and Vector Relationships," *Annu. Rev. of Phytopathol* 30:315–348 (1992); van Poelwijk et al., "Replication and Expression of the Tospovirus Genome. Proceedings of the International Symposium on Tospovirus and Thrips of Floral and Vegetable Crops," *Acta Horticulturae* 431:201–208 (1996)). Based on serological properties, vector specificity, host range, and nucleotide and amino acid sequences of the nucleoprotein gene, several species have been established in the genus Tospovirus (de Ávila et al., "Classification of Tospoviruses Based on Phylogeny of Nucleoprotein Gene Sequences," *J. Gen. Virol* 74:153–159 (1993); Goldbach et al., "Introduction. In: International Symposium on Tospoviruses and Thrips of Floral and Vegetable Crops," *Acta Horticulturae* 431:21–26 (1996); Peters et al., "Vector Relations in the Transmission and Epidemiology of Tospoviruses. In: International Symposium on Tospoviruses and Thrips of Floral and Vegetable Crops," *Acta Horticulturae* 431:29–42 (1996)). Tomato spotted wilt virus (TSWV), tomato chlorotic spot virus (TCSV), impatiens necrotic spot virus (INSV), and groundnut ringspot virus (GRSV) are the Tospovirus species commonly associated with important yield losses in the tomato crop. TSWV, the type species of the genus, has a worldwide distribution, whereas GRSV and TCSV have, thus far, only been identified on tomatoes grown in Brazil and Argentina (Dewey et al., "Molecular Diversity of Tospovirus in Argentina: A Summary. In: International Symposium on Tospoviruses and Thrips of Floral and Vegetable Crops," *Acta Horticulturae* 431:261–263 (1996); Peters et al., "Vector Relations in the Transmission and Epidemiology of Tospoviruses. In: International Symposium on Tospoviruses and Thrips of Floral and Vegetable Crops," *Acta Horticulturae* 431:29–42 (1996); Resende et al., "New Tospovirus Species Found in Brazil. In: International Symposium on Tospoviruses and Thrips of Floral and Vegetable Crops," *Acta Horticulturae* 431:78–89 (1996)). In Brazil, new tospovirus species that infect tomato are also being characterized (Resende et al., "New Tospovirus Species Found in Brazil. In: International Symposium on Tospoviruses and Thrips of Floral and Vegetable Crops," *Acta Horticulturae* 431:78–89 (1996)).

Because genetic resistance offers the best means of protecting crop plants against tospovirus infection, considerable effort has been devoted to the development of resistant varieties (Cho et al., "Conventional Breeding: Host-Plant Resistance and the Use of Molecular Markers to Develop Resistance to Tomato Spotted Wilt Virus in Vegetables. In: International Symposium on Tospoviruses and Thrips of Floral and Vegetable Crops," *Acta Horticulturae* 431:367–378 (1996); Roselló et al., "Genetics of Tomato Spotted Wilt Virus Resistance Coming From *Lycopersicon peruvianum*," *Eur. J. of Plant Path.* 104:499–509 (1998)). Naturally occurring host resistance to tospoviruses has been reported in many Lycopersicon species (Finlay, "Inheritance of Spotted Wilt Resistance in Tomato. II. Five Genes Controlling Spotted Wilt Resistance in Four Tomato Types," *Aust. J. Biol. Sci.* 6:153–163 (1953); Cho et al., "Conventional Breeding: Host-Plant Resistance and the Use of Molecular Markers to Develop Resistance to Tomato Spotted Wilt Virus in Vegetables. In: International Symposium on Tospoviruses and Thrips of Floral and Vegetable Crops," *Acta Horticulturae* 431:367–378 (1996); Krishna Kumar et al., "Evaluation of Lycopersicum Germplasm for Tomato Spotted Wilt Tospovirus Resistance by Mechanical and Thrips Transmission," *Plant Dis.* 77:938–941 (1993); Paterson et al., "Resistance in Two Lycopersicon Species to an Arkansas Isolate of Tomato Spotted Wilt Virus," *Euphytica* 43:173–178 (1989); Roselló et al., "Viral Diseases Causing the Greatest Economic Losses to the Tomato Crop. I. The Tomato Spotted Wilt Virus—A Review," *Scientia Horticulturae* 67:117–150 (1996); Stevens et al., "Evaluation of Seven Lycopersicon Species for Resistance to Tomato Spotted Wilt Virus (TSWV)," *Euphytica* 80:79–84 (1994)). However, in many cases, this resistance is species and/or isolate specific and therefore not very useful for breeding purposes. Broad spectrum tospovirus resistance was found in the *L. esculentum* cultivar 'Stevens' (van Zijl et al., "Breeding Tomatoes for Processing in South Africa," *Acta Horticulturae* 194:69–75 (1986)). The TSWV resistance of this cultivar, introgressed from an unknown *L. peruvianum* accession, is conferred by a single gene, Sw-5, which is incompletely dominant (Stevens et al., "Inheritance of a Gene for Resistance to Tomato Spotted Wilt Virus (TSWV) From *Lycopersicon peruvianum* Mill," *Euphytica* 59:9–17 (1992)). This gene also seems to provide resistance to TCSV and GRSV (Boiteux et al., "Genetic Basis of Resistance Against Two Tospovirus Species in Tomato (*Lycopersicon esculentum*)," *Euphytica* 71:151–154 (1993)).

Genes conferring resistance to different isolates of the same pathogen or different pathogens are often organized in the plant genome as tandem arrays of homologues (Hammond-Kosack et al., "Plant Disease Resistance Genes," *Annu. Rev. Plant Physiol. Plant Mol. Biol.* 48:575–607 (1997)). Therefore, the multiple resistances conferred by Sw-5 raise the question of whether the Sw-5 locus consists of a cluster of tightly linked genes, each gene having its own virus specificity, or whether it encodes a single gene product capable of recognizing several tospovirus isolates and species. In addition, the physiological mechanism by which Sw-5 provides resistance is unclear. In tomato plants carrying Sw-5, the virus cannot spread systemically throughout the plant; and, in many cases, the inoculated leaves do not show any macroscopic symptoms. However, for some tospovirus isolates and/or under high inoculum pressure, local and systemic necrotic lesions appear on the inoculated plants, suggesting that Sw-5 resistance can elicit a hypersensitive response (Stevens et al., "Inheritance of a Gene for Resistance to Tomato Spotted Wilt Virus (TSWV) From *Lycopersicon peruvianum* Mill," *Euphytica* 59:9–17 (1992); Brommonschenkel et al., "Map-based Cloning of the Tomato Genomic Region that Spans the Sw-5 Tospovirus Resistance Gene in Tomato," *Mol. Gen. Genet.* 256:121–126 (1997); Roselló et al., "Genetics of Tomato Spotted Wilt Virus Resistance Coming From *Lycopersicon peruvianum*," *Eur. J. of Plant Path.* 104:499–509 (1998)). Sw-5 may also be developmentally regulated, as the resistance gene does not appear to provide tospovirus resistance in tomato fruits (de Haan et al., "Transgenic Tomato Hybrids Resistant to Tomato Spotted Wilt Virus Infection. In: International Symposium on Tospoviruses, and Thrips of Floral and Vegetable Crops," *Acta Horticulturae* 431:417–426 (1996)).

These unusual characteristics of Sw-5 and its tight linkage to RFLP marker CT220 on the long arm of tomato chromosome 9 led to the isolation of this gene via map-based cloning. By high resolution-genetic linkage analysis of Sw-5 recombinant plants and chromosome walking, it was demonstrated that the Sw-5 locus resides in a 100 kb genomic region spanned by 10 overlapping plant transformation-competent cosmid clones (Brommonschenkel et al., "Map-based Cloning of the Tomato Genomic Region that Spans the Sw-5 Tospovirus Resistance Gene in Tomato," *Mol. Gen. Genet* 256:121–126 (1997); Tanksley et al, "High Density Molecular Linkage Maps of the Tomato and Potato Genomes," *Genetics* 132:1141–1160 (1992)).

Tospoviruses causes substantial yield losses to ornamental and vegetable crops worldwide. TSWV is especially damaging to tomatoes in South America, Africa, and certain parts of Asia. No genes conferring resistance to this virus have been isolated. It would be useful to have a Tospovirus resistance gene in order to engineer virus resistant tomatoes and other crops.

The present invention is directed to overcoming this and related deficiencies in the art.

SUMMARY OF THE INVENTION

The present invention relates to an isolated plant nucleic acid molecule which imparts resistance in plants to Tospoviruses.

The present invention also relates to a protein, which may be purified or recombinant, which is encoded by the isolated nucleic acid of the present invention.

The present invention also relates to a method of imparting to a plant resistance to a Tospovirus which involves transforming a plant with a nucleic acid molecule under conditions effective to impart to the plant resistance to a Tospovirus.

The present invention also relates to a method of eliciting a hypersensitive response in a plant. This involves providing a transgenic plant which has been transformed with a nucleic acid molecule which imparts resistance in plants to Tospoviruses, and expressing the nucleic acid under conditions to elicit a hypersensitive response in the plant.

BRIEF DESCRIPTION OF THE DRAWINGS

FIG. 1A shows the alignment of cosmid clones in the chromosome region around the RFLP marker CT220 that contains Sw-5, based on high resolution genetic linkage analysis. Horizontal lines represent the cosmid inserts contained within 10 overlapping cosmid clones. The circled letters R and S identify cosmid clones that either confer resistance (R) or fail to confer resistance (S) to tospoviruses upon mechanical inoculation. FIG. 1B shows fine mapping of Sw-5 inside cosmid TC134 by complementation analysis. Cosmid clone TC53 that overlaps with TC134 and lacks the TCD1-homologous region (horizontal line) fails to complement the susceptible phenotype of Moneymaker. Later sequence analysis showed that the genomic region containing Sw-5 (shown as diagonal lines) is truncated in both non-complementing cosmids TC53 and TC55.

FIGS. 4A–C show expression and structure of the Sw-5 gene. FIG. 4A is blot analysis of Sw-5 RNA. Polyadenylated RNA from leaves of the cultivars SW-99-1 (R, 10 μg) and Piedmont (S, 10 μg) were fractionated on a 1.3% agarose gel containing formaldehyde, blotted onto Hybond N$^+$ membrane, hybridized with radiolabeled TCD1 insert and exposed to Kodak X-AR film for 7 days. FIG. 4B shows the Sw-5 homologous genomic region of cosmid TC134 and transcript represented as solid black boxes. The angled lines indicate the intron. FIG. 4C shows the deduced Sw-5 protein sequence (SEQ. ID. No. 2). Boundaries of the NBS conserved region are indicated. The polypeptide regions corresponding to kinase-1a, kinase-2, and kinase-3 motifs and two other conserved domains discussed in the text are underlined. The leucine-rich repeat ("LRR") region is represented in italics.

FIGS. 5A–C show a detailed analysis of the Sw-5 deduced protein structure. FIG. 5A is a amphiphilicity profile of the Sw-5 protein. FIG. 5B shows a comparison of the conserved centrally located Sw-5 NBS domain (SEQ. ID. No. 3) with: Mil.2 (SEQ. ID. No. 4), Prf (SEQ. ID. No. 5), Rx (SEQ. ID. No. 6), I2C-1 (SEQ. ID. No. 7), and I2C-2 (SEQ. ID. No. 8) and RPM1 (SEQ. ID. No. 9). The conserved kinase-1a, kinase-2, kinase-3a and the conserved hydrophobic domain are indicated. FIG. 5C shows comparisons of the LRR domains of Sw-5 (SEQ. ID. No. 10), Mi-1.2 (SEQ. ID. No. 11), and Prf (SEQ. ID. No. 12). Black boxes in a column indicate identical or similar amino acids.

DETAILED DESCRIPTION OF THE INVENTION

Figure 1:
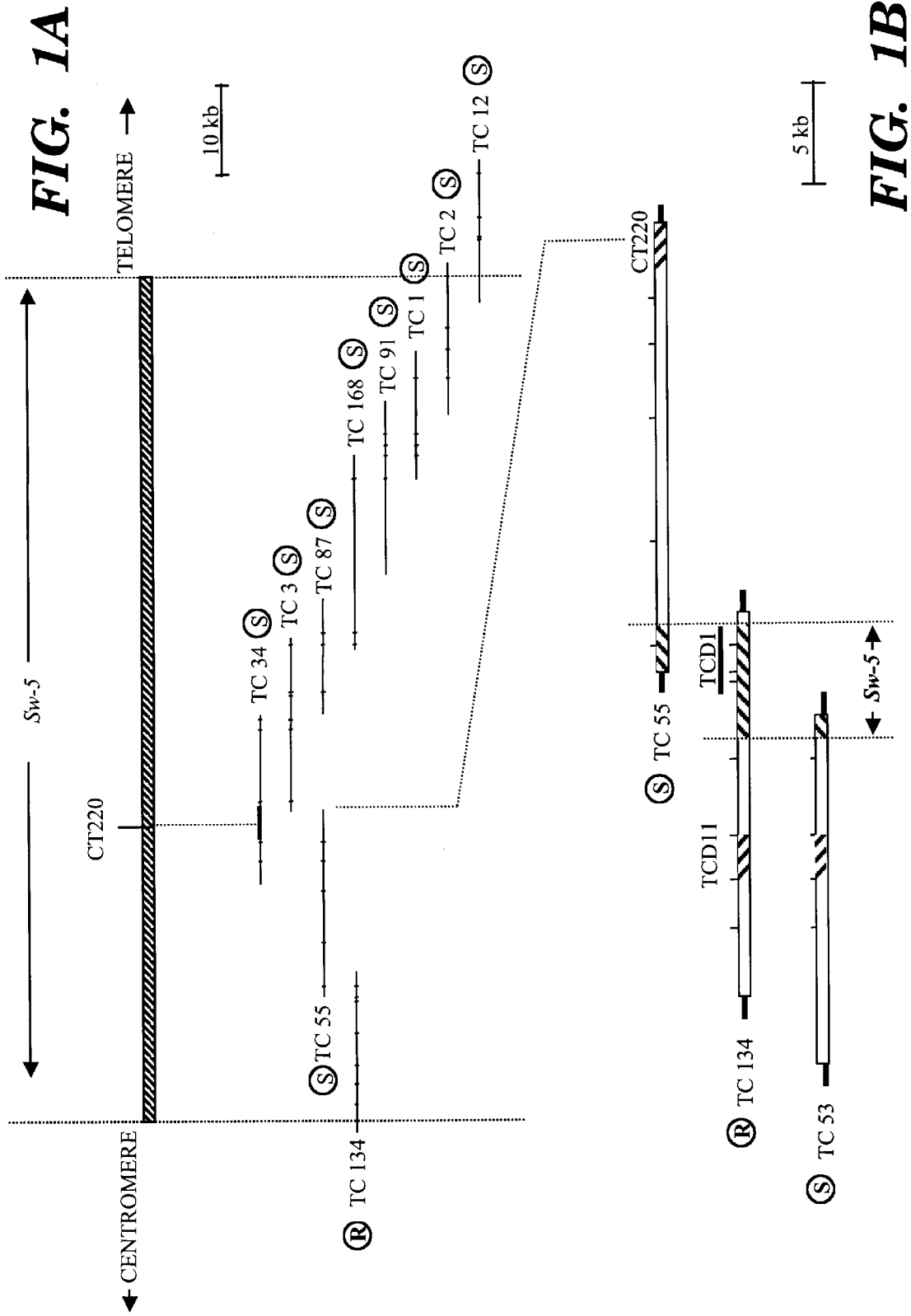
FIGS. 1A–B show the positional cloning of the Sw-5 Tospovirus resistance locus.

The present invention relates to an isolated plant nucleic acid molecule which imparts resistance in plants to Tomato Spotted Wilt Virus. One suitable form of the nucleic acid of the present invention is the SW-5 gene isolated from tomato which has a nucleic acid sequence corresponding to SEQ. ID. No. 1 as follows:

```
atggctgaaa atgaaattga ggaaatgtta gagcacctga gaaggatcaa gagtggaggt      60
gatctggatt ggctcgacat attgcgaatt gaagaacttg aaatggtgct aagagttttt     120 agaacccttta caaagtatca tgatgttctt ttgcctgatt ccttagtcga actcacaaag    180
agggccaaat tgactgggga atacttcac cgggtgttgg gtaggattcc acataaatgt      240
aaaactaacc ttaatctgga aaggctagaa tcacatttgt tggaattctt tcaaggtaat    300
acggcaagtt taagtcacaa ttatgagttg aatgattttg atctgtcgaa atatatggat    360
tgtctggaaa attttctaaa tgatgtactg atgatgttct tgcaaaagga taggttcttc    420
cattccagag aacaacttgc aaaacatcga tcaataaagg aactgaaaat tgttcaaaag    480
aaaataagat ttttgaaata catatatgcc acagagataa atggttatgt cgactatgag    540
aagcaggaat gtttggagaa tcgaattcag ttcatgacta cactgtggg acaatattgt      600 ttggcagtat tagattatgt cactgagggt aaacttaatg aagaaaatga caactttagt    660
aaacctcctt accttatatc attgattgtg ttagtggagc tggaaatgaa gaagattttt    720
catggtgaag taaaggcttc aaagtttact caatcaaaaa ctttcaagga caagaaatta    780
ccaaaaggat tttcacatca tctccacaat ctgttgatgt atctcagaaa caaaaagctc    840
gagaattttc ctaataatat cgctgctcaa atattgatg tggcaataga gttcttgttg      900
gttttccttg atgctgatgt gtcaaatcat gttattaatg gtaactggtt gaaaaaggtc    960
ttgttaaagg ttggagctat agcgggtgat attctatatg taattcaaaa gcttcttcct   1020
agatcaataa acaaagatga aactagcaac ataagtcttt gctcaataca gatattggag   1080
aagactaaag atctgaaggc acaagttgag acgtactaca aatccttaaa atttactcca   1140
tctcagttcc ccacctttgg tggattgagc tttctgaatt ctcttttaag gaaactgaat   1200
gagatgtcga catctaagtc cggattaggt ttcctgatga aacctctttt agggaatttg   1260
gagaaagagc tatcatctct tacatccatt ttagagaagg agctctcatc cattttccgt   1320
gatgtcgtgc accatgaaca taacattcct aaagatcttc agaggcgtac catcaatttg   1380
tcatatgagg ctgaggttgc tattgattct attcttgctc agtataatgc ttttttgcat   1440 atttttttgct cacttcctac aattgtaaaa gagatcaagc aaattaatgc agaggtgact   1500
gagatgtggt cagcggacat tcctcttaat cctcactatg tggctgctcc attaaaacat   1560
ctgccggatc gacatagcaa tcttgtaact gatgaggagg tagtgggttt tgagaataaa   1620
gcagaagaac taattgatta tctgattaga ggtacaaatg agctagacgt tgtcccaatt   1680
gtaggcatgg gaggacaagg gaaaacgaca attgctagaa agttgtacaa taatgacatt   1740
attgtttctc gctttgatgt tcgagcatgg tgcatcattt ctcaaacgta taatcggaga   1800
gagttattac aagatatttt cagtcaagtt acaggttccg acgacaatgg agctacggtt   1860
gatgttcttg ccgacatgtt gaggagaaaa ttaatgggaa agagatatct cattgtattg   1920
gatgatatgt gggattgtat ggtatgggat gacttaaggc tttcttttcc agatgatgga   1980
attagaagca aatagtcgt aacaactcga cttgaagaag tgggtaagca agtcaagtac    2040
catactgatc cttattctct tccattcctc acaacagaag agagttgcca attgttgcag   2100
aaaaaagtgt ttcaaaagga agattgcccg cctgaactac aagatgtgag tcaagcagta   2160
gcagaaaaat gcaaaggact gcccctagtg gttgtcttgg tagctggaat aatcaaaaaa   2220
aggaaaatgg aagaatcttg gtggaatgag gtgaaagatg ctttatttga ctatcttgac   2280
agtgagttcg aagaatacag tctggcaact atgcagttga gttttgataa cttaccccac   2340
tgtttaaagc cttgtcttct ttatatggga atgttttcgg aggacgcaag aattccagca   2400
```

-continued

```
tctacattga taagtttatg gattgctgaa ggattcgtgg agaacactga atctgggaga    2460
ttaatggaag aggaagctga aggttacttg atggatctca ttagcagtaa cttggtaatg    2520
ctttcaaaga gaacttataa gggtagagtc aaatactgtc aggttcatga tgttgtgcat    2580
cactttgct tggaaaagag tagagaagca aagtttatgc ttgcagtgaa gggtcaatat     2640
atccattttc aaccttcgga ttggaaggga actcgagtga gcttcagttt tagtgaagag    2700
ctttccaagt ttgcatctct ggtctccaaa acacagaagc ctttccatca acacttgagg    2760
tcattgataa cgaccaatcg agcaaaatct attaatgata ttttctcctg tcagattagt    2820
gaattgcgac ttcttaaagt cttggatttg agttcttata ttgtggagtt tttgtcgtta    2880
gctacattca aaccactaaa tcagctgaag tacctcgcag ttcaggcttt tgaattctat    2940
tttgatccag gatcacatct tccccatata gaaactttca ttgtaatgaa tcttccttat    3000
tatgatatat tgttaccagt gtcttttttgg gaaatgaaaa aattaaggca tgctcatttt   3000
ggtaaggctg aatttgacaa gcaggggctc tctgaaggat cctctaaatt ggaaaatttg    3120
aggatattaa agaatattgt tggatttgat agggtggatg tgttatcaag gaggtgtcct    3180
aatcttcaac aacttcaaat cacatatttt gggaataatg aagagccttt ttgtcccaaa    3240
ttggagaatc ttacccagct tcaacaactt caactttcct ttgcgcgtcc ccgcactcta    3300
tccgggttac agttgccttc aaatttaaat aagttggtac ttgaaggaat tcatatagaa    3360
agtgttattc ccttcattgc gggactacca agcctggaat atctccaatt acaggatgtg    3420
tgttttcctc aatcagaaga gtggtgcctt ggagatatca cgttccataa acttaagttg    3480
ttgaaactgg taaagttaaa tatatcaagg tgggatgtct cagaggaatc atttccgttg    3540
cttgaaacac tcgttataaa gaagtgcatt gacctagagg agatcccact tagctttgct    3600
gatattccaa cattggaaca gattaaattg attgggtcct ggaaagtatc tctggaggat    3660
tcagctgtga gaatgaagga agaaatcaaa gacactgaag gatgtgatcg tttacacctc    3720
gtcaaacaac gctcagattg a                                              3741
```

The present invention also relates to a protein encoded by the plant nucleic acid molecule, which, in accordance with the present invention, imparts resistance in plants to Tospoviruses. An example of such a protein is the SW-5 protein, encoded by the nucleotide corresponding to SEQ. ID. NO. 1. This protein has an amino acid sequence corresponding to SEQ. ID. No. 2, as follows:

```
Met Ala Glu Asn Glu Ile Glu Glu Met Leu Glu His Leu Arg Arg Ile
 1               5                  10                  15

Lys Ser Gly Gly Asp Leu Asp Trp Leu Asp Ile Leu Arg Ile Glu Glu
                20                  25                  30

Leu Glu Met Val Leu Arg Val Phe Arg Thr Phe Thr Lys Tyr His Asp
                35                  40                  45

Val Leu Leu Pro Asp Ser Leu Val Glu Leu Thr Lys Arg Ala Lys Leu
            50                  55                  60

Thr Gly Glu Ile Leu His Arg Val Leu Gly Arg Ile Pro His Lys Cys
65                  70                  75                  80

Lys Thr Asn Leu Asn Leu Glu Arg Leu Glu Ser His Leu Leu Glu Phe
                85                  90                  95

Phe Gln Gly Asn Thr Ala Ser Leu Ser His Asn Tyr Glu Leu Asn Asp
                100                 105                 110

Phe Asp Leu Ser Lys Tyr Met Asp Cys Leu Glu Asn Phe Leu Asn Asp
                115                 120                 125
```

-continued

```
Val Leu Met Met Phe Leu Glu Lys Asp Arg Phe Phe His Ser Arg Glu
        130                 135                 140
Gln Leu Ala Lys His Arg Ser Ile Lys Glu Leu Lys Ile Val Gln Lys
145                 150                 155                 160
Lys Ile Arg Phe Leu Lys Tyr Ile Tyr Ala Thr Gln Ile Asn Gly Tyr
                165                 170                 175
Val Asp Tyr Glu Lys Gln Glu Cys Leu Glu Asn Arg Ile Gln Phe Met
            180                 185                 190
Thr Asn Thr Val Gly Gln Tyr Cys Leu Ala Val Leu Asp Tyr Val Thr
        195                 200                 205
Gln Gly Lys Leu Asn Glu Glu Asn Asp Asn Phe Ser Lys Pro Pro Tyr
    210                 215                 220
Leu Leu Ser Leu Ile Val Leu Val Gln Leu Glu Met Lys Lys Ile Phe
225                 230                 235                 240
His Gly Glu Val Lys Ala Ser Lys Phe Thr Gln Ser Lys Thr Phe Lys
                245                 250                 255
Asp Lys Lys Leu Pro Lys Gly Phe Ser His His Leu His Asn Leu Leu
            260                 265                 270
Met Tyr Leu Arg Asn Lys Lys Leu Glu Asn Phe Pro Asn Asn Ile Ala
        275                 280                 285
Ala Gln Asn Ile Asp Val Ala Ile Gln Phe Leu Leu Val Phe Leu Asp
    290                 295                 300
Ala Asp Val Ser Asn His Val Ile Asn Gly Asn Trp Leu Lys Lys Val
305                 310                 315                 320
Leu Leu Lys Val Gly Ala Ile Ala Gly Asp Ile Leu Tyr Val Ile Gln
                325                 330                 335
Lys Leu Leu Pro Arg Ser Ile Asn Lys Asp Gln Thr Ser Asn Ile Ser
            340                 345                 350
Leu Cys Ser Ile Gln Ile Leu Glu Lys Thr Lys Asp Leu Lys Ala Gln
        355                 360                 365
Val Gln Thr Tyr Tyr Lys Ser Leu Lys Phe Thr Pro Ser Gln Phe Pro
    370                 375                 380
Thr Phe Gly Gly Leu Ser Phe Leu Asn Ser Leu Leu Arg Lys Leu Asn
385                 390                 395                 400
Gln Met Ser Thr Ser Lys Ser Gly Leu Gly Phe Leu Met Lys Pro Leu
                405                 410                 415
Leu Gly Asn Leu Glu Lys Glu Leu Ser Ser Leu Thr Ser Ile Leu Glu
            420                 425                 430
Lys Glu Leu Ser Ser Ile Phe Arg Asp Val Val His Glu His Asn
        435                 440                 445
Ile Pro Lys Asp Leu Gln Arg Arg Thr Ile Asn Leu Ser Tyr Glu Ala
    450                 455                 460
Glu Val Ala Ile Asp Ser Ile Leu Ala Gln Tyr Asn Ala Phe Leu His
465                 470                 475                 480
Ile Phe Cys Ser Leu Pro Thr Ile Val Lys Glu Ile Lys Gln Ile Asn
                485                 490                 495
Ala Glu Val Thr Glu Met Trp Ser Ala Asp Ile Pro Leu Asn Pro His
            500                 505                 510
Tyr Val Ala Ala Pro Leu Lys His Leu Pro Asp Arg His Ser Asn Leu
        515                 520                 525
Val Thr Asp Glu Glu Val Val Gly Phe Glu Asn Lys Ala Glu Glu Leu
    530                 535                 540
```

-continued

```
Ile Asp Tyr Leu Ile Arg Gly Thr Asn Glu Leu Asp Val Val Pro Ile
545                 550                 555                 560

Val Gly Met Gly Gly Gln Gly Lys Thr Thr Ile Ala Arg Lys Leu Tyr
                565                 570                 575

Asn Asn Asp Ile Ile Val Ser Arg Phe Asp Val Arg Ala Trp Cys Ile
                580                 585                 590

Ile Ser Gln Thr Tyr Asn Arg Arg Glu Leu Leu Gln Asp Ile Phe Ser
            595                 600                 605

Gln Val Thr Gly Ser Asp Asp Asn Gly Ala Thr Val Asp Val Leu Ala
            610                 615                 620

Asp Met Leu Arg Arg Lys Leu Met Gly Lys Arg Tyr Leu Ile Val Leu
625                 630                 635                 640

Asp Asp Met Trp Asp Cys Met Val Trp Asp Asp Leu Arg Leu Ser Phe
                645                 650                 655

Pro Asp Asp Gly Ile Arg Ser Arg Ile Val Val Thr Thr Arg Leu Glu
                660                 665                 670

Gln Val Gly Lys Gln Val Lys Tyr His Thr Asp Pro Tyr Ser Leu Pro
            675                 680                 685

Phe Leu Thr Thr Glu Glu Ser Cys Gln Leu Leu Gln Lys Lys Val Phe
690                 695                 700

Gln Lys Glu Asp Cys Pro Pro Glu Leu Gln Asp Val Ser Gln Ala Val
705                 710                 715                 720

Ala Glu Lys Cys Lys Gly Leu Pro Leu Val Val Leu Val Ala Gly
                725                 730                 735

Ile Ile Lys Lys Arg Lys Met Glu Glu Ser Trp Trp Asn Glu Val Lys
                740                 745                 750

Asp Ala Leu Phe Asp Tyr Leu Asp Ser Glu Phe Glu Tyr Ser Leu
            755                 760                 765

Ala Thr Met Gln Leu Ser Phe Asp Asn Leu Pro His Cys Leu Lys Pro
            770                 775                 780

Cys Leu Leu Tyr Met Gly Met Phe Ser Glu Asp Ala Arg Ile Pro Ala
785                 790                 795                 800

Ser Thr Leu Ile Ser Leu Trp Ile Ala Glu Gly Phe Val Gln Asn Thr
                805                 810                 815

Gln Ser Gly Arg Leu Met Glu Glu Ala Glu Gly Tyr Leu Met Asp
                820                 825                 830

Leu Ile Ser Ser Asn Leu Val Met Leu Ser Lys Arg Thr Tyr Lys Gly
            835                 840                 845

Arg Val Lys Tyr Cys Gln Val His Asp Val Val His His Phe Cys
850                 855                 860

Leu Glu Lys Ser Arg Glu Ala Lys Phe Met Leu Ala Val Lys Gly Gln
865                 870                 875                 880

Tyr Ile His Phe Gln Pro Ser Asp Trp Lys Gly Thr Arg Val Ser Phe
                885                 890                 895

Ser Phe Ser Glu Glu Leu Ser Lys Phe Ala Ser Leu Val Ser Lys Thr
                900                 905                 910

Gln Lys Pro Phe His Gln His Leu Arg Ser Leu Ile Thr Thr Asn Arg
            915                 920                 925

Ala Lys Ser Ile Asn Asp Ile Phe Ser Cys Gln Ile Ser Glu Leu Arg
            930                 935                 940

Leu Leu Lys Val Leu Asp Leu Ser Ser Tyr Ile Val Glu Phe Leu Ser
945                 950                 955                 960
```

-continued

```
Leu Ala Thr Phe Lys Pro Leu Asn Gln Leu Lys Tyr Leu Ala Val Gln
            965                 970                 975

Ala Phe Glu Phe Tyr Phe Asp Pro Gly Ser His Leu Pro His Ile Glu
            980                 985                 990

Thr Phe Ile Val Met Asn Leu Pro Tyr Tyr Asp Ile Leu Leu Pro Val
        995                 1000                1005

Ser Phe Trp Glu Met Lys Lys Leu Arg His Ala His Phe Gly Lys Ala
    1010                1015                1020

Glu Phe Asp Lys Gln Gly Leu Ser Glu Gly Ser Ser Lys Leu Glu Asn
1025                1030                1035                1040

Leu Arg Ile Leu Lys Asn Ile Val Gly Phe Asp Arg Val Asp Val Leu
            1045                1050                1055

Ser Arg Arg Cys Pro Asn Leu Gln Gln Leu Gln Ile Thr Tyr Phe Gly
            1060                1065                1070

Asn Asn Glu Glu Pro Phe Cys Pro Lys Leu Glu Asn Leu Thr Gln Leu
        1075                1080                1085

Gln Gln Leu Gln Leu Ser Phe Ala Arg Pro Arg Thr Leu Ser Gly Leu
        1090                1095                1100

Gln Leu Pro Ser Asn Leu Asn Lys Leu Val Leu Glu Gly Ile His Ile
1105                1110                1115                1120

Glu Ser Val Ile Pro Phe Ile Ala Gly Leu Pro Ser Leu Glu Tyr Leu
            1125                1130                1135

Gln Leu Gln Asp Val Cys Phe Pro Gln Ser Glu Glu Trp Cys Leu Gly
            1140                1145                1150

Asp Ile Thr Phe His Lys Leu Lys Leu Leu Lys Leu Val Lys Leu Asn
            1155                1160                1165

Ile Ser Arg Trp Asp Val Ser Glu Glu Ser Phe Pro Leu Leu Glu Thr
    1170                1175                1180

Leu Val Ile Lys Lys Cys Ile Asp Leu Glu Glu Ile Pro Leu Ser Phe
1185                1190                1195                1200

Ala Asp Ile Pro Thr Leu Glu Gln Ile Lys Leu Ile Gly Ser Trp Lys
            1205                1210                1215

Val Ser Leu Glu Asp Ser Ala Val Arg Met Lys Glu Glu Ile Lys Asp
        1220                1225                1230

Thr Glu Gly Cys Asp Arg Leu His Leu Val Lys Gln Arg Ser Asp
        1235                1240                1245
```

Also suitable for use in the present invention are variants of the nucleic acid molecule shown above. An example of a suitable nucleic acid is a nucleic acid molecule which has a nucleotide sequence which hybridizes to the nucleotide sequence of SEQ. ID. No. 1 under stringent conditions comprising 37° C. in a hybridization buffer of 0.9M sodium citrate.

Fragments of the above protein are also encompassed by the present invention. Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein of the present invention, fragments of the gene of the present invention may be synthesized by using the PCR technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the protein of the present invention. These fragments can then be separated by conventional procedures (e.g., chromatography, SDS-PAGE) and used in the methods of the present invention.

Variants may also (or alternatively) be prepared by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Another aspect of the present invention is an expression vector containing a DNA molecule encoding an SW-5 protein. The nucleic acid molecule of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soil-borne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens*. Fraley, et al., "Expression of Bacterial Genes in Plant Cells," *Proc. Nat'l Acad. Sci.*, 80:4803–4807 (1983), which is hereby incorporated by reference in its entirety.

Further improvement of this technique led to the development of the binary vector system. Bevan, M., "Binary Agrobacterium Vectors for Plant Transformation," *Nucleic Acids Res.* 12:8711–8721 (1984), which is hereby incorporated by reference in its entirety. In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19. Frisch, et al., "Complete Sequence of the Binary Vector Bin19," *Plant Molec. Biol.* 27:405–409 (1995), which is hereby incorporated by reference in its entirety. Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

In one aspect of the present invention, the nucleic acid molecule of the present invention is incorporated into an appropriate vector in the sense direction, such that the open reading frame is properly oriented for the expression of the encoded protein under control of a promoter of choice.

Certain "control elements" or "regulatory sequences" are also incorporated into the vector-construct. Those non-translated regions of the vector, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens*, (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference in its entirety). Expression of the Sw-5 protein is induced in the plants transformed with the Sw-5 gene when the transgenic plants are brought into contact with nanomolar concentrations of a glucocorticoid, or by contact with dexamethasone, a glucocorticoid analog. Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference in their entirety. In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety).

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature* 313(6005):810–812 (1985), which is hereby incorporated by reference in its entirety). Virtually any 3' regulatory region known to be operable in plants would suffice for proper expression of the coding sequence of the DNA construct of the present invention.

The vector of choice, promoter, and an appropriate 3' regulatory region can be ligated together to produce the plasmid of the present invention using well known molecular cloning techniques as described in Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant cell. Basically, this method is carried out by transforming a plant cell with the nucleic acid of the present invention under conditions effective to yield transcription of the nucleic acid molecule in the plant cell. Preferably, the nucleic acid molecule of the present invention is stably inserted into the genome of the recombinant plant cell as a result of the transformation.

One approach to transforming plant cells with the nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA,* 79:1859–63 (1982), which is hereby incorporated by reference in its entirety).

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. In one embodiment of the present invention transformants are generated using the method of Frary et al, *Plant Cell Reports* 16: 235 (1996), which is hereby incorporated by reference in its entirety, to transform seedling explants.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coli* that encodes the β-glucuronidase protein, also known as GUS. Jefferson et al., "GUS Fusions: β Glucuronidase as a Sensitive and Versatile Gene Fusion Marker in Higher Plants," *EMBO Journal* 6:3901–3907 (1987), which is hereby incorporated by reference in its entirety. GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

Other suitable selection markers include, without limitation, markers encoding for antibiotic resistance, such as the nptII gene which confers kanamycin resistance (Fraley, et al., *Proc. Natl. Acad. Sci. USA,* 80:4803–4807 (1983), which is hereby incorporated by reference in its entirety) and the dhfr gene, which confers resistance to methotrexate (Bourouis et al., *EMBO J.* 2:1099–1104 (1983), which is hereby incorporated by reference in its entirety).

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

After the nucleic acid molecule of the present invention is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

Another aspect of the present invention is a method of conferring resistance to Tospoviruses. This involves transforming plants with the nucleic acid molecule of the present invention under conditions effective to impart to the plant resistance to Tospoviruses. Transfection, transformation, and regeneration of plants containing the nucleic acid of the present invention can be carried out as described above.

Another aspect of the present invention is a method of eliciting a hypersensitive response in plants. This involves transforming plants with a nucleic acid molecule of the present invention, as described above, and expressing the nucleic acid under conditions effective to elicit a hypersensitive response. The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise*, Vol. 5, J. G. Horsfall and E. B. Cowling, ed. Academic Press New York (1980); Klement, Z., "Hypersensitivity," pages 149–177 in: *Phytopathogenic Prokaryotes*, Vol. 2, M. S. Mount and G. H. Lacy, ed. Academic Press, New York (1982), which are hereby incorporated by reference in their entirety). The localized cell death contains the infecting pathogen from spreading further.

EXAMPLES

Example 1

Figure 2:
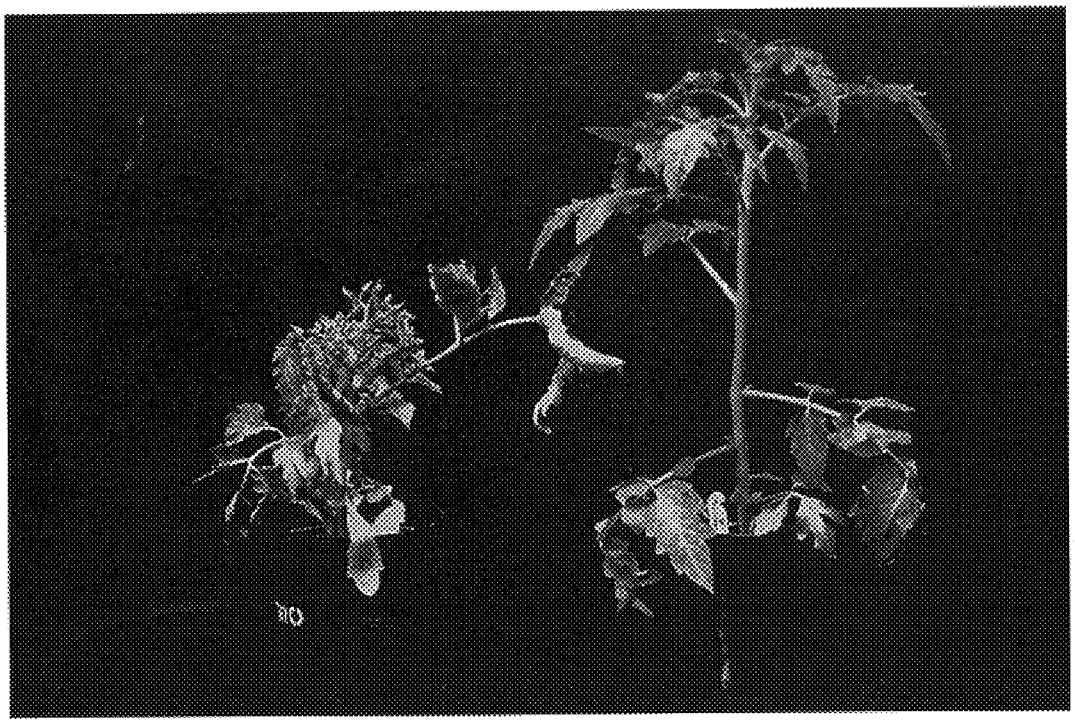
FIG. 2 shows genetic complementation with Cosmid Clone TC134. Symptoms of a systemic infection in an untransformed Moneymaker plant are shown in the plant on the left, and resistance response of a Moneymaker plant transformed with cosmid TC134 can be seen in the plant on the right.

Complementation Experiments: Location of the Sw-5 Locus Within a 20 kb Cosmid Clone Earlier work narrowed down the location of Sw-5 to a 100 kb segment of tomato chromosome 9 spanned by the 10 overlapping plant transformation-competent cosmid clones shown in FIG. 1A (Brommonschenkel et al., "Map-based Cloning of the Tomato Genomic Region that Spans the Sw-5 Tospovirus Resistance Gene in Tomato," *Mol. Gen. Genet* 256:121–126 (1997); Tanksley et al, "High Density Molecular Linkage Maps of the Tomato and Potato Genomes," *Genetics* 132:1141–1160 (1992), which are hereby incorporated by reference it their entirety). To further refine the position of Sw-5 within this contig, the cosmid clones were transferred into *Agrobacterium tumefaciens* and used to transform the TSWV susceptible tomato cultivar 'Moneymaker." For each cosmid, 3 to 10 independent transformants were generated. The primary transformants were selfed and 20–30 progeny of each T1 plant were screened separately for resistance to TSWV, GRSV, and TCSV isolates in the greenhouse. All of the progeny plants, except those derived from transgenic plants carrying cosmid TC134 (insert ~20 kb), were completely susceptible to the tospovirus species and isolates. In contrast, progeny plants derived from Moneymaker: TC134 transformants showed a hypersensitive-like response to TSWV and no symptoms to GRSV and TCSV on inoculated leaves. These transgenic plants, resembled the control plants carrying Sw-5 in that systemic, invasion did not occur, as seen in FIG. 2. DAS-ELISA tests using uninoculated apical leaf samples from these plants confirmed the absence of the viruses. PCR analysis indicated a perfect correlation between tospovirus resistance and the presence of TC134 cosmid sequences. Progeny plants that were not carrying TC134 (due to normal segregation) showed typical tospovirus symptoms such as stunting and general necrosis. Overall, these results indicate that all Sw-5 specificity resides on the cosmid TC134.

Example 2

Molecular Cloning of the Sw-5 Gene

Figure 3:
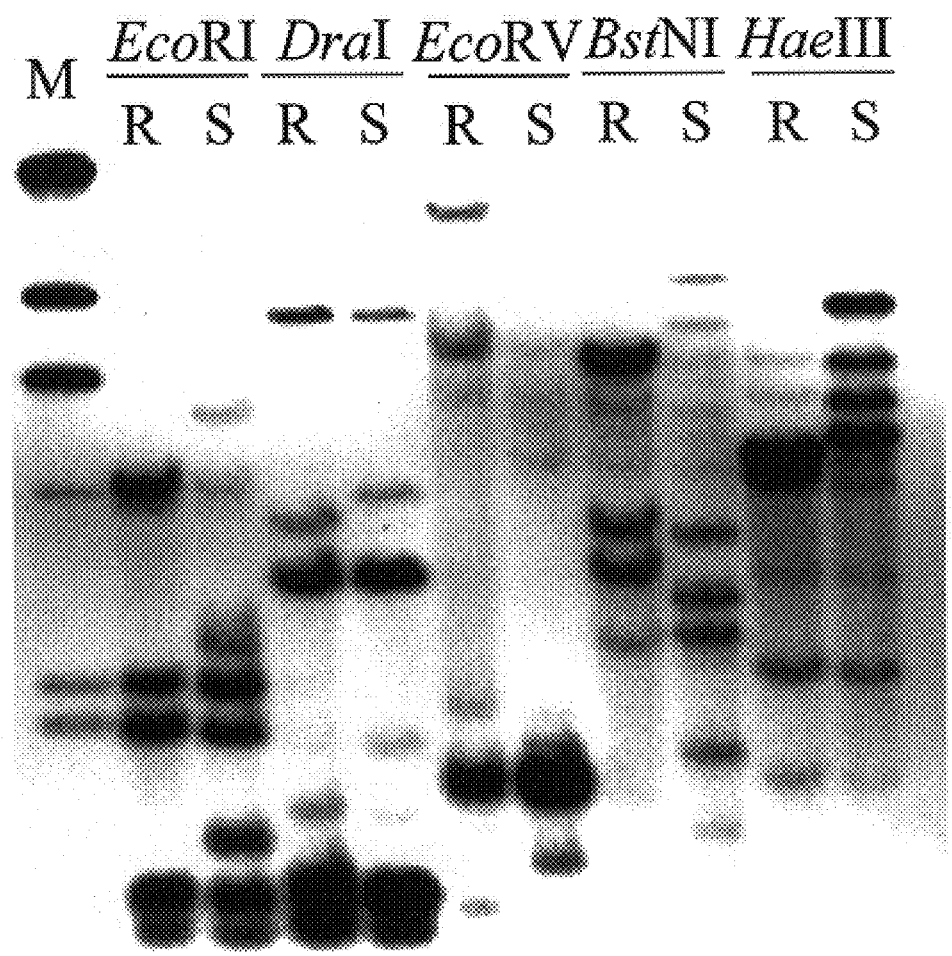
FIG. 3 is a Southern blot analysis of cDNA clone TCD1. Genomic DNA from tomato cultivars SW99-1 (R) and Piedmont (S) was isolated from leaves. Aliquots of 3 μg were digested with the indicated enzymes, separated by electrophoresis on a 1% agarose gel, blotted onto Hybond N$^+$ membrane and hybridized with radiolabeled TCD1 insert. The first line (M) represents the molecular length standard λ Hind III.

To identify candidates for the Sw-5 gene from the TC134 genomic region, a leaf cDNA library constructed from the susceptible cultivar Mogeor was probed with TC134 subclones. Two different cDNAs were obtained, TCD1 (~2.2 kb) and TCD11 (~1.2 kb). Sequence analysis revealed that the predicted TCD1 protein product has regions of homology with known plant disease resistance proteins; showing the greatest similarity to the tomato gene Prf(Salmeron et al., "Tomato Prf is a Member of the Leucine-Rich Repeat Class of Plant Disease Resistance Genes and Lies Embedded Within the Pto Kinase Gene Cluster," *Cell* 86:123–133 (1996), which is hereby incorporated by reference it its entirety. In contrast, TCD11 showed no homology with known plant resistance (R) genes. DNA gel blot analysis, shown in FIG. 3, demonstrated that while TCD11 is single copy, numerous TCD1-related sequences are present in the tomato genome. This result suggested that TCD1 was a member of a multigene family. This finding correlates well with previous studies which indicate that plant R genes often occur in gene families (Hammond-Kosack et al., "Plant Disease Resistance Genes," *Annu. Rev. Plant Physiol. Plant Mol. Biol.* 48:575–607 (1997); Staskawicz et al., "Molecular Genetics of Plant Disease Resistance," *Science* 268(5211)

:661–667 (1995), which is hereby incorporated by reference it its entirety). From these two lines of evidence, TCD1 appeared to be the most likely candidate for Sw-5. To prove that TCD1 was indeed derived from the Sw-5 locus, additional transformation experiments were performed with another cosmid clone, TC53, which does not cross hybridize to TCD1 but does contain the remainder of the genomic DNA in TC134 (FIG. 1B). Three independent transgenic Moneymaker plants were obtained, selfed, and their progenies analyzed for tospovirus, resistance. All plants were found to be completely susceptible, leading to the conclusion that Sw-5 lies in the region corresponding to TCD1.

Example 3

Expression and Structure of the Sw-5 Gene

Figures 4A, 4B:
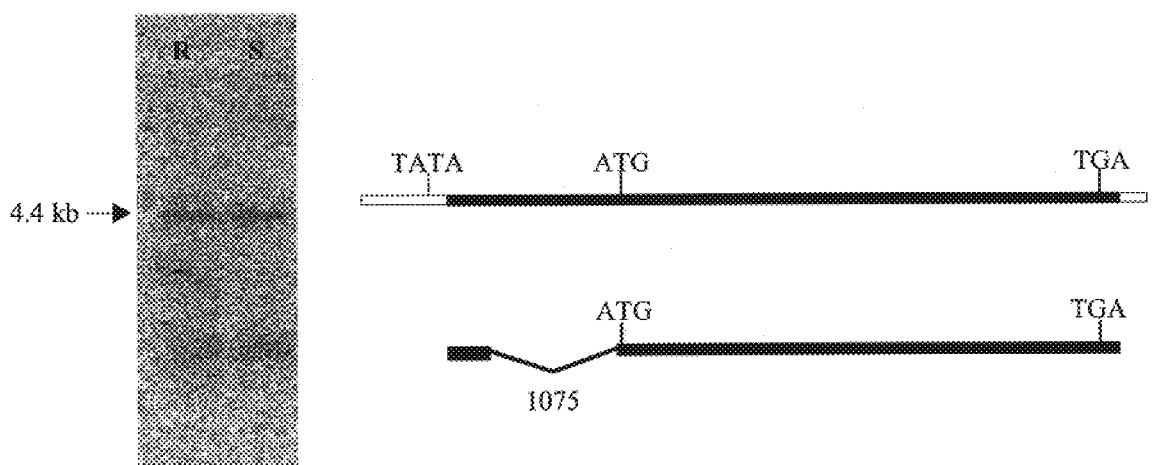

Gel blots containing poly(A)+ RNA isolated from the leaves of susceptible and resistant tomato lines were hybridized with TCD1. FIG. 4A shows that a weakly expressed transcript of ~4.4 kb was detected in both resistant and susceptible plants. Given that the TCD1 cDNA is only 2.2 kb, this result suggests that TCD1 is derived from a truncated Sw-5 transcript. Sequencing of the region of the TC134 cosmid which hybridizes to TCD1 and an additional ~4.0 kb upstream of the 5' end of this cDNA, identified only one large, intronless, open reading frame (ORF) of 3738 base pairs (bp), encoding a putative hydrophilic polypeptide of 1246 amino acid residues with a relative molecular mass of 144 kDa (FIG. 4B).

The complete structure of Sw-5 was determined by characterizing additional cDNAs derived from a size-selected unidirectional cDNA library constructed from leaf tissue of the Sw-5 homozygous line SW99-1. After screening 3×10$^6$ primary cDNA clones using TCD1 as a probe, 16 hybridizing cDNA clones were identified. Isoline DNA blotting analysis, restriction mapping, and sequence analysis revealed that six clones corresponded to Sw-5, whereas the other ten corresponded to at least three additional genes with a similar sequence. The longest Sw-5 cDNA clone was 3.9 kb. The longest insert in the other five Sw-5 homologous cDNA clones was only 2.6 kb. However, when organized together, these cDNA clones produce a deduced transcribed sequence of ~4172 bp, which is close to the size of the Sw-5 mRNA as determined by RNA blot analysis, shown in FIG. 4A. Comparison of the cDNA and genomic sequences revealed the presence of an intron (~1075 nt) in the 5' untranslated region of Sw-5, shown in FIG. 4B. Thus, the processed transcript has a 5' untranslated region of ~234 nucleotides. The length of the 5' untranslated region is 160 nucleotides. The nucleotides flanking the putative Sw-5 translation start site (GAAAATGGC) are consistent with the consensus sequence for translation initiation in plants (AACAAUGGC; Lütcke et al., "Selection of AUG Initiation Codons Differs in Plants and Animals," *EMBO J.* 6:43–48 (1987), which is hereby incorporated by reference it its entirety, and several in-frame stop codons are located upstream of the start codon. A typical TATA box sequence is present 1523 bases upstream of the start codon. The polyadenylation signal is located 135 nucleotides downstream of the termination codon.

The deduced amino acid sequence of Sw-5 is shown in FIG. 4C. The Sw-5 sequence shows the greatest similarity to the amino acid sequence of the nematode resistance protein Mi and the protein required for Pseudomonas resistance and fenthion sensitivity, Prf. The Sw-5 protein contains many motifs found in previously cloned R genes: a putative nucleotide binding site ("NBS") composed of kinase-1a (or P loop, amino acids 562 to 571), kinase-2a (amino acids 634 to 644), and putative kinase-3a (amino acids 663 to 670) domains (Grant et al., "Structure of the Arabidopsis RPMI Gene Enabling Dual Specificity Disease Resistance," *Science* 269:843–846 (1995); Hammond-Kosack et al., "Plant Disease Resistance Genes," *Annu. Rev. Plant Physiol. Plant Mol. Biol.* 48:575–607 (1997), which are hereby incorporated by reference it their entirety). An additional motif of unknown function is present (amino acids 774 to 785) that is well-conserved in the products of other R genes (Grant et al., "Structure of the Arabidopsis RPM1 Gene Enabling Dual Specificity Disease Resistance," *Science* 269:843–846 (1995); Hammond-Kosack et al., "Plant Disease Resistance Genes," *Annu. Rev. Plant Physiol. Plant Mol. Biol.* 48:575–607 (1997), which are hereby incorporated by reference it their entirety). The C-terminal region of Sw-5 is composed of 14 imperfect LRRs, beginning at amino acid 916, as shown in FIG. 4C.

Figure 5A:
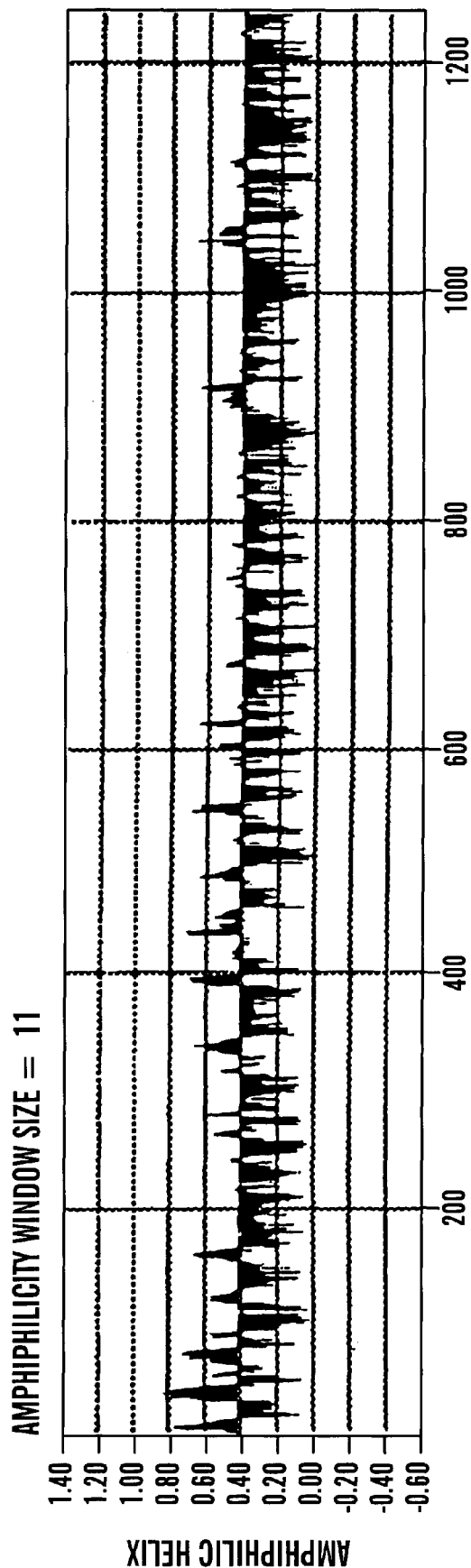

FIGS. 5A–C show a detailed analysis of the Sw-5 deduced protein structure. FIG. 5A is a amphiphilicity profile of the Sw-5 protein. FIG. 5B shows a comparison of the conserved centrally located Sw-5 NBS domain (SEQ. ID. No. 3) with other known resistance genes: tomato Mi-1.2 (SEQ. ID. No. 4) (Milligan et al., "The Root Knot Nematode Resistance Gene Mi from Tomato Is A Member of the Leucine Zipper, Nucleotide Binding, Leucine-Rich Repeat Family of Plant Resistance Genes, *Plant Cell* 10: 1307–1319 (1998), which is hereby incorporated by reference in its entirety), tomato Prf (SEQ. ID. No. 5) (Salmeron et al., "Tomato Prf is a Member of the Leucine-Rich Repeat Class of Plant Disease Resistance Genes and Lies Embedded Within the Pto Kinase Gene Cluster," *Cell* 86:123–133 (1996), which is hereby incorporated by reference in its entirety), potato virus X resistance gene Rx (SEQ. ID. No. 6) (van der Voort et al., "Tight Physical Linkage of the Nematode Resistance Gene Gpa2 and the Virus Resistance Gene Rx On A Single Segment Introgressed From the Wild Species *Solanum tuberosum* subsp. andigena CPC 1673 Into Cultivated Potato," *Mol Plant-Microbe Interact.* 12:197–206 (1999), which is hereby incorporated by reference in its entirety), tomato I2C-1 (SEQ. ID. No. 7) and I2C-2 (SEQ. ID. No. 8) (Ori et al., "The I2C Family From the Wilt Disease Resistance Locus I2 Belongs to the Nucleotide-Binding, Leucine-Rich Repeat Family of Plant Resistance Genes," *Plant Cell* 9(4):521–32 (1997), which is hereby incorporated by reference in its entirety) and Arabidopsis RPM1 (SEQ. ID. No. 9) (Grant et al., "Structure of the Arabidopsis RPM1 Gene Enabling Dual Specificity Disease Resistance," *Science* 269:843–846 (1995) which is hereby incorporated by reference in its entirety). The conserved kinase-1a, kinase-2, kinase-3a and the conserved hydrophobic domain are indicated. FIG. 5C shows comparisons of the LRR domains of Sw-5 (SEQ. ID. No. 10), Mi-1.2 (SEQ. ID. No. 11), and Prf (SEQ. ID. No. 12). Black boxes in a column indicate identical or similar amino acids.

Example 4

Mechanism of TSWV Resistance

The NBS-LRR class of R proteins have one common feature: they mediate the development of cell death at sites of infection. Thus, the similarity of Sw-5 to these proteins supports the possibility that the mechanism of TSWV resistance involves the elicitation of a hypersensitive response. For example, the resistance to root knot provided by the Mi gene, which is the R gene with the greatest similarity to Sw-5, is characterized by a localized necrosis near the site where feeding cells would normally be initiated (Dropkin, "Physiology of Nematodes of the Soil," *An. N.Y. Acad. Sci.* 139(1):39–52 (1966), which is hereby incorporated by reference it its entirety). The fact that the hypersensitive response is not always observed in a Sw-5 background may be due to differences in the affinity of the tospovirus elicitor to Sw-5 and/or differences in the timing of the interaction.

The Sw-5 protein is remarkably similar to the Mi protein. With the exception of the four heptad amphiphatic leucine zippers at the N-terminus that are not evident in Sw-5, the similarity is dispersed over the entire molecule. It seems reasonable to hypothesize that the functionally and structurally related Sw-5 and Mi proteins may act through a common signal transduction pathway. As root-knot nematodes (Williamson et al., "Nematode Pathogenesis and Resistance in Plants," *Plant Cell* 8(10):1735–1745 (1996), which is hereby incorporated by reference it its entirety) and viruses probably secrete/produce several proteins inside the plant cell as part of their life cycles/pathogenic strategies, the similarity of Sw-5 to Mi is not surprising and probably reflects the remarkable epitope-recognition ability and signal transduction activation of NBS-LRR proteins.

Example 5

Genomic Distribution of the Sw-5 Gene Family

Figure 6:
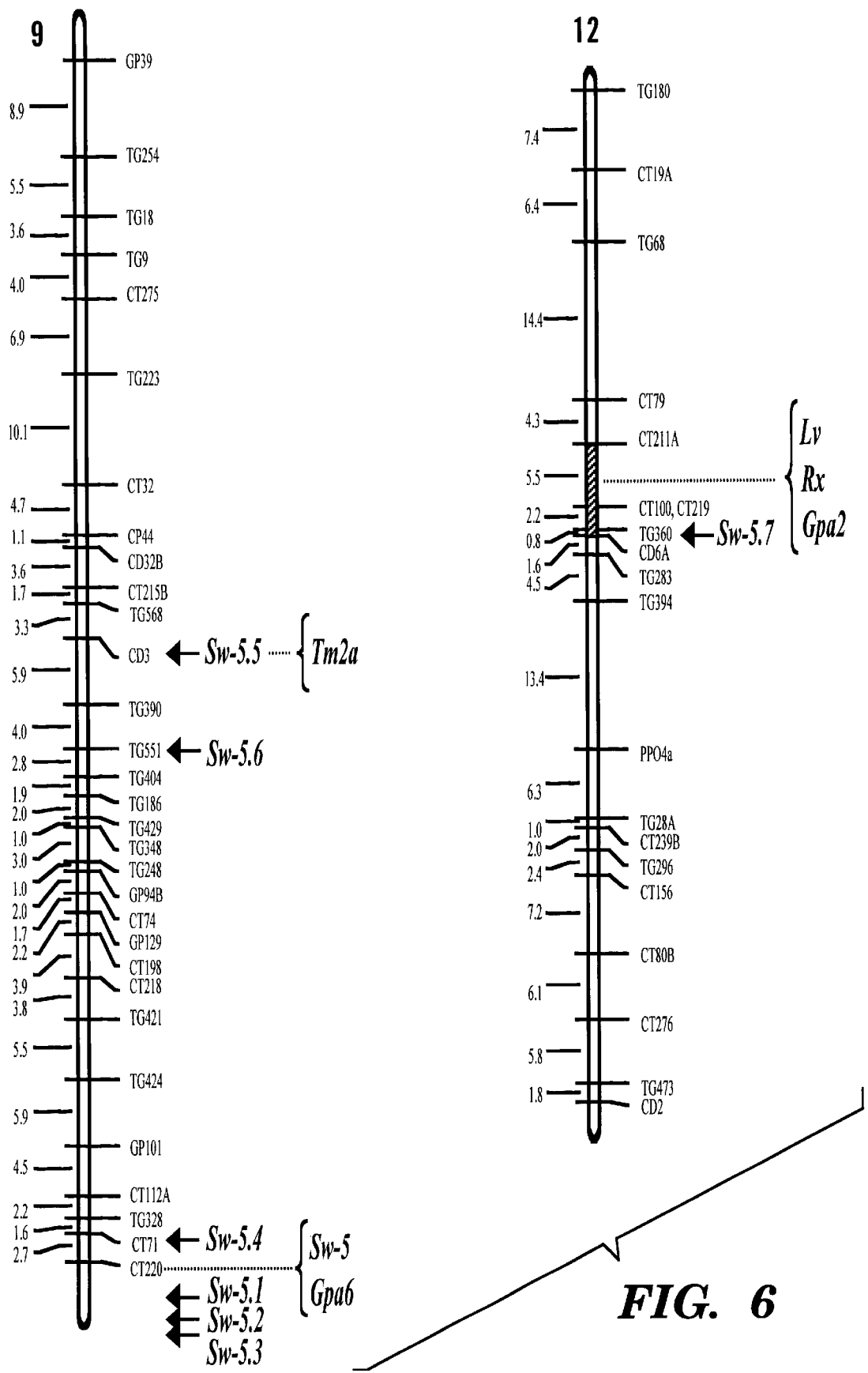
FIG. 6 shows linkage maps of chromosome 9 and 12 showing the distribution of Sw-5 homologues in the tomato genome.

Cosmid DNA blot analysis did not reveal any additional copies of Sw-5 in the 150 kb cosmid contig around the Sw-5 locus (Brommonschenkel et al., "Map-based Cloning of the Tomato Genomic Region that Spans the Sw-5 Tospovirus Resistance Gene in Tomato," *Mol. Gen. Genet* 256:121–126 (1997); Tanksley et al, "High Density Molecular Linkage Maps of the Tomato and Potato Genomes," *Genetics* 132:1141–1160 (1992); Tanksley et al., "Seed Banks and Molecular Maps: Unlocking Genetic Potential from the Wild," *Science* 277(5329):1063–1066 (1997), which are hereby incorporated by reference it their entirety). Because the cDNA screening and isoline DNA blot analysis suggested that Sw-5 was a member of a multigene family, the chromosomal positions of the homologous sequences were assessed by RFLP mapping in an *L. esculentum*×*L. pennellii* $F_2$ mapping population (Tanksley et al, "High Density Molecular Linkage Maps of the Tomato and Potato Genomes," *Genetics* 132:1141–1160 (1992), which is hereby incorporated by reference it its entirety). As shown in FIG. 6, most of the Sw-5 homolog sequences are dispersed on tomato chromosome 9. Four Sw-5 homolog sequences map to the telomeric region of chromosome 9: Sw-5.1, Sw-5.2 and Sw-5.3 map 3.6, 5.7, and 6.3 cM below CT220, respectively. This is the site of the *Globodera pallida* resistance gene Gpa6 in the homologous potato genome (van der Voort, "Mapping Genetic Factors Controlling Potato/Cyst Nematode Interactions, Ph.D. Thesis," Wageningen Agricultural University, Wageningen, The Netherlands (1998), which is hereby incorporated by reference it its entirety). The fourth homolog, Sw-5.4, cosegregates with CT71, located 2.7 cM above CT220. Two other two homologs map on chromosome 9 in the vicinity of the TM2a tobacco mosaic virus R gene (Pillen et al, "Construction of a High-Resolution Genetic Map and YAC-Contigs in the Tomato Tm-2a Region," *Theor. Appl. Genet.* 93:998–233 (1996), which is hereby incorporated by reference it its entirety): Sw-5.5 cosegregates with CD3, just below the centromeric region and Sw-5.6 maps with TG551 further down the long arm of chromosome 9. The Sw-5.7 homolog maps to chromosome 12, cosegregating with TG360, the same region where the powdery mildew resistance gene Lv has been mapped (Chunwongse et al., "High Resolution Map of the Lv Resistance Locus in Tomato," *Theor. Appl. Genet.* 95:220–223 (1997), which is hereby incorporated by reference it its entirety). Clearly, Sw-5 is a member of a multigene family whose members are dispersed throughout the tomato genome and may be conferring resistance to a variety of pathogens.

Example 6

Tospovirus Resistance Evaluation

Tospovirus resistance was evaluated by mechanical inoculations. The tospovirus strains used for the inoculation tests were: BR-01, 'HR' (TSWV), V1-3 and BR-03 (TCSV), and SA-05 (GRSV). The original inoculum was kept at −80° C. and thawed prior to multiplication in *Nicotiana tabacum* cv Havana 425. Inoculum was prepared by macerating young, newly infected Havana 425 leaves with a mortar and pestle in 0.1M potassium phosphate buffer, pH 7.0, containing 0.01M sodium sulfite. The leaves of tomato plants at the 3- to 5-leaf stage (approximately 30–37 days after germination) were dusted with 600 mesh carborundum powder and the inoculum was applied with cheesecloth. A second inoculation was done 2 to 3 days after the first. Plants were evaluated weekly for symptoms and held in the greenhouse for at least 6 weeks after infection. Inoculations consistently resulted in 100% infection of the susceptible tomato control cv. 'Piedmont'.

All inoculated plants were assayed for the presence of the virus using the double antibody sandwich enzyme-linked immunoabsorbent assay (DAS-ELISA) (Cho et al., 1988, which is hereby incorporated by reference it its entirety) and species-specific polyclonal antisera. Symptomatic tissues from plants were sampled and tested for tospovirus. Plants not exhibiting systemic infection were held in the greenhouse for 6 weeks after which time leaf samples from the middle and top of the plants were removed and tested for tospovirus infection.

Example 7

RFLP Analysis

The standard $F_2$ mapping population (VF36 Tm2a× *Lycopersicon pennellii*) was employed in determining the map location of TCD1 homologous sequences essentially as described by Tanksley et al, "High Density Molecular Linkage Maps of the Tomato and Potato Genomes," *Genetics* 132:1141–1160 (1992), which is hereby incorporated by reference in its entirety.

Example 8

DNA Sequencing and Computer Analysis

DNA sequences were determined from double-stranded plasmid DNA by the dideoxy chain termination method using Sequenase 2.0 (USB, Cleveland, Ohio). Sequencing reaction products were run on a automated sequencer (ABI 310 and ABI 377 Sequencer, Applied Biosystems, Foster City, Calif.). The DNA sequences were assembled using MacVector (International Biotechnology). Homology searches of GeneBank database were performed using the BLAST 2.0 algorithm (Altschul et al., "Gapped BLAST and PSI-BLAST: A New Generation of Protein Database Search Programs," *Nucleic Acids Res.* 25:3389–3402 (1997), which is hereby incorporated by reference in its entirety). Alignments with other sequences were performed using the MegAlign program (DNASTAR).

Example 9

Plant Transformation

Cosmid clones were introduced into *Agrobacterium tumefaciens* strain LBA4404 by triparental mating or electroporation. Transformation of excised cotyledons from susceptible tomato cultivar Moneymaker was conducted essentially as described by Frary et al., "An Examination of Factors Affecting the Efficiency of Agrobacterium-Mediated Transformation of Tomato," *Plant Cell Rep.* 16:235–240 (1996), which is hereby incorporated by reference in its entirety. Transgenic plants were identified by resistance to kanamycin and confirmed by PCR assays using specific primers that distinguished between the transgenic cosmid insert and endogenous sequences. Positive transformants, were transferred to the greenhouse and selfed. The T1 progeny were analyzed for virus resistance by mechanical inoculation.

Example 10 cDNA Library Construction and Screening

Total RNA was isolated from unchallenged leaves of the Sw99-1 line and poly(A)+ RNA was purified using the Oligotex mRNA maxi-preparation kit (QIAgen, Germany). Double stranded cDNA was synthesized using oligo(dT) as primer. After addition of EcoRI linkers, the cDNA molecules were size fractionated. Pools that contained molecules longer than 2.0 kb were combined and ligated to λZapII vector linearized with EcoRI and XhoI, encapsidated in vitro and amplified in *E. coli* strain XL1-Blue according to the supplier's instructions (Stratagene, La Jolla, Calif.).

Approximately $3 \times 10^6$ primary recombinants were screened using the cDNA clone TCD1 as a probe. Hybridizations were performed at 65° C. according to the method of Church and Gilbert, "Genomic Sequencing," *Proc. Natl. Acad. Sci USA*, 81(7): 1991–1995 (1984), which is hereby incorporated by reference in its entirety). Filters were washed three times at 65° C., once with 2×SSC, 0.1% SDS, once with 1×SSC, 0.1% SDS and once with 0.5% SSC, 0.1% SDS, for 20 min. each. After plaque purification, selected positive phage clones were converted to pBluescript SK-phagemid clones using helper phage and following the supplier's instructions (Stratagene, La Jolla, Calif.).

Example 11

RNA Gel Blot Analysis

RNA was fractionated on a 1% agarose-0.66 M formaldehyde gel. RNA species were transferred to nylon membranes (Hybond-N$^+$, Amersham, UK) by capillary action using 10×SSC. After NaOH fixation, filters were hybridized at 65° C. according to the method of Church et al., "Genomic Sequencing," *Proc. Natl. Acad. Sci. USA* 81(7): 1991–1995 (1984), which is hereby incorporated by reference in its entirety). Filters were washed three times at 65° C., once with 2× SSC, 0.1% SDS, once with 1×SSC, 0.1% SDS and once with 0.5% SSC, 0.1% SDS, for 20 min. each. A 0.24 to 9.5-kb RNA ladder (Gibco-BRL, Bethesda, Md.) was used as the size reference.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated plant nucleic acid molecule which imparts resistance in plants to a Tospovirus and is a nucleotide-binding site-leucine-rich repeat resistance gene, wherein the nucleic acid molecule consists essentially of either: 1) a nucleotide sequence that encodes a protein having the amino acid sequence of SEQ ID NO: 2 or 2) the nucleotide sequence of SEQ ID NO: 1.

2. The isolated nucleic acid molecule according to claim 1, wherein the Tospovirus is selected from a group consisting of Tomato Spotted Wilt Virus, Tomato Chlorotic Spot Virus, Impatiens Necrotic Spot Virus, and Groundnut Ringspot Virus.

3. The isolated nucleic acid molecule according to claim 1, wherein the nucleic acid molecule is a DNA molecule.

4. An expression vector containing the nucleic acid molecule according to claim 1.

5. The expression vector according to claim 4, wherein the nucleic acid molecule is incorporated in the expression vector in sense orientation.

6. A host cell transformed with the nucleic acid molecule according to claim 1, wherein the cell is a plant cell or a bacterial cell.

7. A transgenic plant transformed with the nucleic acid molecule according to claim 1.

8. The transgenic plant according to claim 7, wherein the plant is tomato.

9. A transgenic plant seed transformed with the nucleic acid molecule according to claim 1.

10. The transgenic plant seed according to claim 9, wherein the plant is tomato.

11. A method of imparting to a plant resistance to a Tospovirus comprising:
transforming a plant with the nucleic acid molecule according to claim 1 under conditions effective to impart to the plant resistance to a Tospovirus.

12. The method according to claim 11, wherein the plant is tomato.

13. A method of eliciting hypersensitive response in plants comprising:
providing a transgenic plant transformed with the plant nucleic acid molecule according to claim 1 and expressing the nucleic acid molecule under conditions effective to elicit a hypersensitive response, wherein said conditions comprise contacting the transgenic plant with a Tospovirus.

14. The method according to claim 13, wherein the plant is tomato.

15. The isolated nucleic acid molecule according to claim 1, wherein the nucleic acid molecule consists essentially of a nucleotide sequence that encodes a protein having the amino acid sequence of SEQ ID NO: 2.

16. The isolated nucleic acid molecule according to claim 1, wherein the nucleic acid molecule consists essentially of the nucleotide sequence of SEQ ID NO: 1.

17. The transgenic plant according to claim 7, wherein the nucleic acid molecule consists essentially of a nucleotide sequence that encodes a protein having the amino acid sequence of SEQ ID NO: 2.

18. The transgenic plant according to claim 7, wherein the nucleic acid molecule consists essentially of the nucleotide sequence of SEQ ID NO: 1.

19. The transgenic plant seed according to claim 9, wherein the nucleic acid molecule consists essentially of a nucleotide sequence that encodes a protein having the amino acid sequence of SEQ ID NO: 2.

20. The transgenic plant seed according to claim 9, wherein the nucleic acid molecule consists essentially of the nucleotide sequence of SEQ ID NO: 1.

21. The method according to claim 11, wherein the nucleic acid molecule consists essentially of a nucleotide sequence that encodes a protein having the amino acid sequence of SEQ ID NO: 2.

22. The method according to claim 11, wherein the nucleic acid molecule consists essentially of the nucleotide sequence of SEQ ID NO: 1.

23. The method according to claim 13, wherein the nucleic acid molecule consists essentially of a nucleotide sequence that encodes a protein having the amino acid sequence of SEQ ID NO: 2.

24. The method according to claim 13, wherein the nucleic acid molecule consists essentially of the nucleotide sequence of SEQ ID NO: 1.

* * * * *

SEQUENCE LISTING

```
<160> NUMBER OF SEQ ID NOS: 12

<210> SEQ ID NO 1
<211> LENGTH: 3741
<212> TYPE: DNA
<213> ORGANISM: Lycopersicon var.

<400> SEQUENCE: 1
atggctgaaa atgaaattga ggaaatgtta gagcacctga gaaggatcaa gagtggaggt      60
gatctggatt ggctcgacat attgcgaatt gaagaacttg aaatggtgct aagagttttt     120 agaacctta caaagtatca tgatgttctt ttgcctgatt ccttagtcga actcacaaag     180
agggccaaat tgactgggga aatacttcac cgggtgttgg gtaggattcc acataaatgt     240
aaaactaacc ttaatctgga aaggctagaa tcacatttgt tggaattctt tcaaggtaat     300
acggcaagtt taagtcacaa ttatgagttg aatgattttg atctgtcgaa atatatggat     360
tgtctggaaa attttctaaa tgatgtactg atgatgttct tgcaaaagga taggttcttc     420
cattccagag aacaacttgc aaaacatcga tcaataaagg aactgaaaat tgttcaaaag     480
aaaataagat ttttgaaata catatatgcc acagagataa atggttatgt cgactatgag     540
aagcaggaat gtttggagaa tcgaattcag ttcatgacta acactgtggg acaatattgt     600
ttggcagtat tagattatgt cactgagggt aaacttaatg aagaaaatga caactttagt     660
```

-continued

```
aaacctcctt acctattatc attgattgtg ttagtggagc tggaaatgaa gaagattttt      720
catggtgaag taaaggcttc aaagtttact caatcaaaaa cttcaagga caagaaatta      780 ccaaaaggat tttcacatca tctccacaat ctgttgatgt atctcagaaa caaaaagctc      840
gagaattttc ctaataatat cgctgctcaa atattgatg tggcaataga gttcttgttg       900
gttttccttg atgctgatgt gtcaaatcat gttattaatg gtaactggtt gaaaaaggtc      960
ttgttaaagg ttggagctat agcgggtgat attctatatg taattcaaaa gcttcttcct    1020
agatcaataa acaaagatga aactagcaac ataagtcttt gctcaataca gatattggag    1080
aagactaaag atctgaaggc acaagttgag acgtactaca aatccttaaa atttactcca    1140
tctcagttcc ccacctttgg tggattgagc tttctgaatt ctcttttaag gaaactgaat    1200
gagatgtcga catctaagtc cggattaggt ttcctgatga aacctctttt agggaatttg    1260
gagaaagagc tatcatctct tacatccatt ttagagaagg agctctcatc cattttccgt    1320
gatgtcgtgc accatgaaca taacattcct aaagatcttc agaggcgtac catcaatttg    1380
tcatatgagg ctgaggttgc tattgattct attcttgctc agtataatgc ttttttgcat    1440 atttttttgct cacttcctac aattgtaaaa gagatcaagc aaattaatgc agaggtgact    1500
gagatgtggt cagcggacat tcctcttaat cctcactatg tggctgctcc attaaaacat    1560
ctgccggatc gacatagcaa tcttgtaact gatgaggagg tagtgggttt tgagaataaa    1620
gcagaagaac taattgatta tctgattaga ggtacaaatg agctagacgt tgtcccaatt    1680
gtaggcatgg gaggacaagg gaaaacgaca attgctagaa agttgtacaa taatgacatt    1740
attgtttctc gctttgatgt tcgagcatgg tgcatcattt ctcaaacgta taatcggaga    1800
gagttattac aagatatttt cagtcaagtt acaggttccg acgacaatgg agctacggtt    1860
gatgttcttg ccgacatgtt gaggagaaaa ttaatgggaa agagatatct cattgtattg    1920
gatgatatgt gggattgtat ggtatgggat gacttaaggc tttcttttcc agatgatgga    1980
attagaagca gaatagtcgt aacaactcga cttgaagaag tgggtaagca agtcaagtac    2040
catactgatc cttattctct tccattcctc acaacagaag agagttgcca attgttgcag    2100 aaaaagtgt ttcaaaagga agattgcccg cctgaactac aagatgtgag tcaagcagta    2160
gcagaaaaat gcaaggact gcccctagtg gttgtcttgg tagctggaat aatcaaaaaa    2220
aggaaaatgg aagaatcttg gtggaatgag gtgaaagatg ctttatttga ctatcttgac    2280
agtgagttcg aagaatacag tctggcaact atgcagttga gttttgataa cttaccccac    2340
tgtttaaagc cttgtcttct ttatatggga atgttttcgg aggacgcaag aattccagca    2400
tctacattga taagtttatg gattgctgaa ggattcgtgg agaacactga atctgggaga    2460
ttaatggaag aggaagctga aggttacttg atggatctca ttagcagtaa cttggtaatg    2520 cttcaaaga gaacttataa gggtagagtc aaatactgtc aggttcatga tgttgtgcat    2580 cactttttgct tggaaaagag tagagaagca aagtttatgc ttgcagtgaa gggtcaatat    2640
atccattttc aaccttcgga ttggaaggga actcgagtga gcttcagttt tagtgaagag    2700
ctttccaagt ttgcatctct ggtctccaaa acacagaagc ctttccatca cacttgagg    2760 tcattgataa cgaccaatcg agcaaaatct attaatgata ttttctcctg tcagattagt    2820
gaattgcgac ttcttaaagt cttggattg agttcttata ttgtggagtt tttgtcgtta    2880
gctacattca aaccactaaa tcagctgaag tacctcgcag ttcaggcttt tgaattctat    2940
tttgatccag gatcacatct tccccatata gaaactttca ttgtaatgaa tcttccttat    3000
tatgatatat tgttaccagt gtcttttttgg gaaatgaaaa aattaaggca tgctcatttt    3060
```

-continued

```
ggtaaggctg aatttgacaa gcaggggctc tctgaaggat cctctaaatt ggaaaatttg   3120
aggatattaa agaatattgt tggatttgat agggtggatg tgttatcaag gaggtgtcct   3180
aatcttcaac aacttcaaat cacatatttt gggaataatg aagagccttt ttgtcccaaa   3240
ttggagaatc ttacccagct tcaacaactt caactttcct ttgcgcgtcc ccgcactcta   3300
tccgggttac agttgccttc aaatttaaat aagttggtac ttgaaggaat tcatatagaa   3360
agtgttattc ccttcattgc gggactacca agcctggaat atctccaatt acaggatgtg   3420
tgttttcctc aatcagaaga gtggtgcctt ggagatatca cgttccataa acttaagttg   3480
ttgaaactgg taaagttaaa tatatcaagg tgggatgtct cagaggaatc atttccgttg   3540
cttgaaacac tcgttataaa gaagtgcatt gacctagagg agatcccact tagctttgct   3600
gatattccaa cattggaaca gattaaattg attgggtcct ggaaagtatc tctggaggat   3660
tcagctgtga aatgaagga agaaatcaaa gacactgaag gatgtgatcg tttacacctc   3720
gtcaaacaac gctcagattg a                                            3741
```

<210> SEQ ID NO 2
<211> LENGTH: 1247
<212> TYPE: PRT
<213> ORGANISM: Lycopersicon var.

<400> SEQUENCE: 2

```
Met Ala Glu Asn Glu Ile Glu Glu Met Leu Glu His Leu Arg Arg Ile
 1               5                  10                  15

Lys Ser Gly Gly Asp Leu Asp Trp Leu Asp Ile Leu Arg Ile Glu Glu
            20                  25                  30

Leu Glu Met Val Leu Arg Val Phe Arg Thr Phe Thr Lys Tyr His Asp
        35                  40                  45

Val Leu Leu Pro Asp Ser Leu Val Glu Leu Thr Lys Arg Ala Lys Leu
    50                  55                  60

Thr Gly Glu Ile Leu His Arg Val Leu Gly Arg Ile Pro His Lys Cys
65                  70                  75                  80

Lys Thr Asn Leu Asn Leu Glu Arg Leu Glu Ser His Leu Leu Glu Phe
                85                  90                  95

Phe Gln Gly Asn Thr Ala Ser Leu Ser His Asn Tyr Glu Leu Asn Asp
            100                 105                 110

Phe Asp Leu Ser Lys Tyr Met Asp Cys Leu Glu Asn Phe Leu Asn Asp
        115                 120                 125

Val Leu Met Met Phe Leu Gln Lys Asp Arg Phe Phe His Ser Arg Glu
    130                 135                 140

Gln Leu Ala Lys His Arg Ser Ile Lys Glu Leu Lys Ile Val Gln Lys
145                 150                 155                 160

Lys Ile Arg Phe Leu Lys Tyr Ile Tyr Ala Thr Glu Ile Asn Gly Tyr
                165                 170                 175

Val Asp Tyr Glu Lys Gln Glu Cys Leu Glu Asn Arg Ile Gln Phe Met
            180                 185                 190

Thr Asn Thr Val Gly Gln Tyr Cys Leu Ala Val Leu Asp Tyr Val Thr
        195                 200                 205

Glu Gly Lys Leu Asn Glu Asn Asp Asn Phe Ser Lys Pro Pro Tyr
    210                 215                 220

Leu Leu Ser Leu Ile Val Leu Glu Leu Glu Met Lys Lys Ile Phe
225                 230                 235                 240

His Gly Glu Val Lys Ala Ser Lys Phe Thr Gln Ser Lys Thr Phe Lys
```

```
                    245                 250                 255
Asp Lys Lys Leu Pro Lys Gly Phe Ser His His Leu His Asn Leu Leu
            260                 265                 270

Met Tyr Leu Arg Asn Lys Lys Leu Glu Asn Phe Pro Asn Asn Ile Ala
        275                 280                 285

Ala Gln Asn Ile Asp Val Ala Ile Glu Phe Leu Leu Val Phe Leu Asp
    290                 295                 300

Ala Asp Val Ser Asn His Val Ile Asn Gly Asn Trp Leu Lys Lys Val
305                 310                 315                 320

Leu Leu Lys Val Gly Ala Ile Ala Gly Asp Ile Leu Tyr Val Ile Gln
                325                 330                 335

Lys Leu Leu Pro Arg Ser Ile Asn Lys Asp Glu Thr Ser Asn Ile Ser
            340                 345                 350

Leu Cys Ser Ile Gln Ile Leu Glu Lys Thr Lys Asp Leu Lys Ala Gln
        355                 360                 365

Val Glu Thr Tyr Tyr Lys Ser Leu Lys Phe Thr Pro Ser Gln Phe Pro
    370                 375                 380

Thr Phe Gly Gly Leu Ser Phe Leu Asn Ser Leu Leu Arg Lys Leu Asn
385                 390                 395                 400

Glu Met Ser Thr Ser Lys Ser Gly Leu Gly Phe Leu Met Lys Pro Leu
                405                 410                 415

Leu Gly Asn Leu Glu Lys Glu Leu Ser Ser Leu Thr Ser Ile Leu Glu
            420                 425                 430

Lys Glu Leu Ser Ser Ile Phe Arg Asp Val Val His His Glu His Asn
        435                 440                 445

Ile Pro Lys Asp Leu Gln Arg Arg Thr Ile Asn Leu Ser Tyr Glu Ala
    450                 455                 460

Glu Val Ala Ile Asp Ser Ile Leu Ala Gln Tyr Asn Ala Phe Leu His
465                 470                 475                 480

Ile Phe Cys Ser Leu Pro Thr Ile Val Lys Glu Ile Lys Gln Ile Asn
                485                 490                 495

Ala Glu Val Thr Glu Met Trp Ser Ala Asp Ile Pro Leu Asn Pro His
            500                 505                 510

Tyr Val Ala Ala Pro Leu Lys His Leu Pro Asp Arg His Ser Asn Leu
        515                 520                 525

Val Thr Asp Glu Glu Val Val Gly Phe Glu Asn Lys Ala Glu Glu Leu
    530                 535                 540

Ile Asp Tyr Leu Ile Arg Gly Thr Asn Glu Leu Asp Val Val Pro Ile
545                 550                 555                 560

Val Gly Met Gly Gly Gln Gly Lys Thr Thr Ile Ala Arg Lys Leu Tyr
                565                 570                 575

Asn Asn Asp Ile Ile Val Ser Arg Phe Asp Val Arg Ala Trp Cys Ile
            580                 585                 590

Ile Ser Gln Thr Tyr Asn Arg Arg Glu Leu Leu Gln Asp Ile Phe Ser
        595                 600                 605

Gln Val Thr Gly Ser Asp Asp Asn Gly Ala Thr Val Asp Val Leu Ala
    610                 615                 620

Asp Met Leu Arg Arg Lys Leu Met Gly Lys Arg Tyr Leu Ile Val Leu
625                 630                 635                 640

Asp Asp Met Trp Asp Cys Met Val Trp Asp Asp Leu Arg Leu Ser Phe
                645                 650                 655

Pro Asp Asp Gly Ile Arg Ser Arg Ile Val Val Thr Thr Arg Leu Glu
            660                 665                 670
```

-continued

```
Glu Val Gly Lys Gln Val Lys Tyr His Thr Asp Pro Tyr Ser Leu Pro
            675                 680                 685

Phe Leu Thr Thr Glu Glu Ser Cys Gln Leu Leu Gln Lys Lys Val Phe
            690                 695                 700

Gln Lys Glu Asp Cys Pro Pro Glu Leu Gln Asp Val Ser Gln Ala Val
705                 710                 715                 720

Ala Glu Lys Cys Lys Gly Leu Pro Leu Val Val Leu Val Ala Gly
                725                 730                 735

Ile Ile Lys Lys Arg Lys Met Glu Glu Ser Trp Trp Asn Glu Val Lys
            740                 745                 750

Asp Ala Leu Phe Asp Tyr Leu Asp Ser Glu Phe Glu Glu Tyr Ser Leu
            755                 760                 765

Ala Thr Met Gln Leu Ser Phe Asp Asn Leu Pro His Cys Leu Lys Pro
            770                 775                 780

Cys Leu Leu Tyr Met Gly Met Phe Ser Glu Asp Ala Arg Ile Pro Ala
785                 790                 795                 800

Ser Thr Leu Ile Ser Leu Trp Ile Ala Glu Gly Phe Val Glu Asn Thr
                805                 810                 815

Glu Ser Gly Arg Leu Met Glu Glu Ala Glu Gly Tyr Leu Met Asp
            820                 825                 830

Leu Ile Ser Ser Asn Leu Val Met Leu Ser Lys Arg Thr Tyr Lys Gly
            835                 840                 845

Arg Val Lys Tyr Cys Gln Val His Asp Val Val His His Phe Cys
850                 855                 860

Leu Glu Lys Ser Arg Glu Ala Lys Phe Met Leu Ala Val Lys Gly Gln
865                 870                 875                 880

Tyr Ile His Phe Gln Pro Ser Asp Trp Lys Gly Thr Arg Val Ser Phe
                885                 890                 895

Ser Phe Ser Glu Leu Ser Lys Phe Ala Ser Leu Val Ser Lys Thr
            900                 905                 910

Gln Lys Pro Phe His Gln His Leu Arg Ser Leu Ile Thr Thr Asn Arg
            915                 920                 925

Ala Lys Ser Ile Asn Asp Ile Phe Ser Cys Gln Ile Ser Glu Leu Arg
            930                 935                 940

Leu Leu Lys Val Leu Asp Leu Ser Ser Tyr Ile Val Glu Phe Leu Ser
945                 950                 955                 960

Leu Ala Thr Phe Lys Pro Leu Asn Gln Leu Lys Tyr Leu Ala Val Gln
                965                 970                 975

Ala Phe Glu Phe Tyr Phe Asp Pro Gly Ser His Leu Pro His Ile Glu
            980                 985                 990

Thr Phe Ile Val Met Asn Leu Pro Tyr Tyr Asp Ile Leu Leu Pro Val
            995                 1000                1005

Ser Phe Trp Glu Met Lys Lys Leu Arg His Ala His Phe Gly Lys Ala
    1010                1015                1020

Glu Phe Asp Lys Gln Gly Leu Ser Glu Gly Ser Ser Lys Leu Glu Asn
    1025                1030                1035                1040

Leu Arg Ile Leu Lys Asn Ile Val Gly Phe Asp Arg Val Asp Val Leu
                1045                1050                1055

Ser Arg Arg Cys Pro Asn Leu Gln Gln Leu Gln Ile Thr Tyr Phe Gly
            1060                1065                1070

Asn Asn Glu Glu Pro Phe Cys Pro Lys Leu Glu Asn Leu Thr Gln Leu
            1075                1080                1085
```

-continued

```
Gln Gln Leu Gln Leu Ser Phe Ala Arg Pro Arg Thr Leu Ser Gly Leu
    1090                1095                1100

Gln Leu Pro Ser Asn Leu Asn Lys Leu Val Leu Glu Gly Ile His Ile
1105                1110                1115                1120

Glu Ser Val Ile Pro Phe Ile Ala Gly Leu Pro Ser Leu Glu Tyr Leu
                1125                1130                1135

Gln Leu Gln Asp Val Cys Phe Pro Gln Ser Glu Trp Cys Leu Gly
            1140                1145                1150

Asp Ile Thr Phe His Lys Leu Lys Leu Leu Lys Leu Val Lys Leu Asn
            1155                1160                1165

Ile Ser Arg Trp Asp Val Ser Glu Glu Ser Phe Pro Leu Leu Glu Thr
        1170                1175                1180

Leu Val Ile Lys Lys Cys Ile Asp Leu Glu Glu Ile Pro Leu Ser Phe
1185                1190                1195                1200

Ala Asp Ile Pro Thr Leu Glu Gln Ile Lys Leu Ile Gly Ser Trp Lys
                1205                1210                1215

Val Ser Leu Glu Asp Ser Ala Val Arg Met Lys Glu Ile Lys Asp
            1220                1225                1230

Thr Glu Gly Cys Asp Arg Leu His Leu Val Lys Gln Arg Ser Asp
        1235                1240                1245

<210> SEQ ID NO 3
<211> LENGTH: 236
<212> TYPE: PRT
<213> ORGANISM: Lycopersicon var.

<400> SEQUENCE: 3

Glu Leu Asp Val Val Pro Ile Val Gly Met Gly Gly Gln Gly Lys Thr
 1               5                  10                  15

Thr Ile Ala Arg Lys Leu Tyr Asn Asn Asp Ile Ile Val Ser Arg Phe
                20                  25                  30

Asp Val Arg Ala Trp Cys Ile Ile Ser Gln Thr Tyr Asn Arg Arg Glu
            35                  40                  45

Leu Leu Gln Asp Ile Phe Ser Gln Val Thr Gly Ser Asp Asp Asn Gly
        50                  55                  60

Ala Thr Val Gly Val Leu Ala Asp Met Leu Arg Arg Lys Leu Met Gly
65                  70                  75                  80

Lys Arg Tyr Leu Ile Val Leu Asp Asp Met Trp Asp Cys Met Val Trp
                85                  90                  95

Asp Asp Leu Arg Leu Ser Phe Pro Asp Asp Gly Ile Arg Ser Arg Ile
            100                 105                 110

Val Val Thr Thr Arg Leu Glu Glu Val Gly Lys Gln Val Lys Tyr His
        115                 120                 125

Thr Asp Pro Tyr Ser Leu Pro Phe Leu Thr Thr Glu Glu Ser Cys Gln
130                 135                 140

Leu Leu Gln Lys Lys Val Phe Gln Lys Glu Asp Cys Pro Pro Glu Leu
145                 150                 155                 160

Gln Asp Val Ser Gln Ala Val Ala Glu Lys Cys Lys Gly Leu Pro Leu
                165                 170                 175

Val Val Val Leu Val Ala Gly Ile Ile Lys Lys Arg Lys Met Glu Glu
            180                 185                 190

Ser Trp Trp Asn Glu Val Lys Asp Ala Leu Phe Asp Tyr Leu Asp Ser
        195                 200                 205

Glu Phe Glu Glu Tyr Ser Leu Ala Thr Met Gln Leu Ser Phe Asp Asn
    210                 215                 220
```

```
Leu Pro His Cys Leu Lys Pro Cys Leu Leu Tyr Met
225                 230                 235
```

<210> SEQ ID NO 4
<211> LENGTH: 235
<212> TYPE: PRT
<213> ORGANISM: Lycopersicon var.

<400> SEQUENCE: 4

```
Asp Leu Asp Val Ile Ser Ile Thr Gly Met Pro Gly Ser Gly Lys Thr
1               5                   10                  15

Thr Leu Ala Tyr Lys Val Tyr Asn Asp Lys Ser Val Ser Arg His Phe
            20                  25                  30

Asp Leu Arg Ala Trp Cys Thr Val Asp Gln Gly Tyr Asp Asp Lys Lys
        35                  40                  45

Leu Leu Asp Thr Ile Phe Ser Gln Val Ser Gly Ser Asp Ser Asn Leu
    50                  55                  60

Ser Glu Asn Ile Asp Val Ala Asp Lys Leu Arg Lys Gln Leu Phe Gly
65                  70                  75                  80

Lys Arg Tyr Leu Ile Val Leu Asp Asp Val Trp Asp Thr Thr Thr Leu
                85                  90                  95

Asp Glu Leu Thr Arg Pro Phe Pro Glu Ala Lys Lys Gly Ser Arg Ile
            100                 105                 110

Ile Leu Thr Thr Arg Glu Lys Glu Val Ala Leu His Gly Lys Leu Asn
        115                 120                 125

Thr Asp Pro Leu Asp Leu Arg Leu Leu Arg Pro Asp Glu Ser Trp Glu
    130                 135                 140

Leu Leu Asp Lys Arg Thr Phe Gly Asn Glu Ser Cys Pro Asp Glu Leu
145                 150                 155                 160

Leu Asp Val Gly Lys Glu Ile Ala Glu Asn Cys Lys Gly Leu Pro Leu
                165                 170                 175

Val Ala Asp Leu Ile Ala Gly Val Ile Ala Gly Arg Glu Lys Lys Arg
            180                 185                 190

Ser Val Trp Leu Glu Val Gln Ser Ser Leu Ser Ser Phe Ile Leu Asn
        195                 200                 205

Ser Glu Val Glu Val Met Lys Val Ile Glu Leu Ser Tyr Asp His Leu
    210                 215                 220

Pro His His Leu Lys Pro Cys Leu Leu His Phe
225                 230                 235
```

<210> SEQ ID NO 5
<211> LENGTH: 236
<212> TYPE: PRT
<213> ORGANISM: Lycopersicon var.

<400> SEQUENCE: 5

```
Glu Leu Asp Val Ile Ser Ile Val Gly Met Pro Gly Leu Gly Lys Thr
1               5                   10                  15

Thr Leu Ala Lys Lys Ile Tyr Asn Asp Pro Glu Val Thr Ser Arg Phe
            20                  25                  30

Asp Val His Ala Gln Cys Val Val Thr Gln Leu Tyr Ser Trp Arg Glu
        35                  40                  45

Leu Leu Leu Thr Ile Leu Asn Asp Val Leu Glu Pro Ser Asp Arg Asn
    50                  55                  60

Glu Lys Glu Asp Gly Glu Ile Ala Asp Glu Leu Arg Arg Phe Leu Leu
65                  70                  75                  80
```

```
Thr Lys Arg Phe Leu Ile Leu Ile Asp Asp Val Trp Asp Tyr Lys Val
                85                  90                  95

Trp Asp Asn Leu Cys Met Cys Phe Ser Asp Val Ser Asn Arg Ser Arg
            100                 105                 110

Ile Ile Leu Thr Thr Arg Leu Asn Asp Val Ala Glu Tyr Val Lys Cys
        115                 120                 125

Glu Ser Asp Pro His His Leu Arg Leu Phe Arg Asp Asp Glu Ser Trp
    130                 135                 140

Thr Leu Leu Gln Lys Glu Val Phe Gln Gly Glu Ser Cys Pro Pro Glu
145                 150                 155                 160

Leu Glu Asp Val Gly Phe Glu Ile Ser Lys Ser Cys Arg Gly Leu Pro
                165                 170                 175

Leu Ser Val Val Leu Val Ala Gly Val Leu Lys Gln Lys Lys Lys Thr
                180                 185                 190

Leu Asp Ser Trp Lys Val Val Glu Gln Ser Leu Ser Ser Gln Arg Ile
            195                 200                 205

Gly Ser Leu Glu Glu Ser Leu Ser Ile Ile Gly Phe Ser Tyr Lys Asn
        210                 215                 220

Leu Pro His Tyr Leu Lys Pro Cys Phe Leu Tyr Phe
225                 230                 235

<210> SEQ ID NO 6
<211> LENGTH: 232
<212> TYPE: PRT
<213> ORGANISM: Solanum tuberosum

<400> SEQUENCE: 6

Glu Leu Glu Val Val Ser Ile Val Gly Met Gly Gly Ile Gly Lys Thr
  1               5                  10                  15

Thr Leu Ala Thr Lys Leu Tyr Ser Asp Pro Cys Ile Met Ser Arg Phe
                20                  25                  30

Asp Ile Arg Ala Lys Ala Thr Val Ser Gln Glu Tyr Cys Val Arg Asn
            35                  40                  45

Val Leu Leu Gly Ile Leu Ser Leu Thr Ser Asp Glu Pro Asp Asp Gln
        50                  55                  60

Leu Ala Asp Arg Leu Gln Lys His Leu Lys Gly Arg Arg Tyr Leu Val
 65                 70                  75                  80

Val Ile Asp Asp Ile Trp Thr Thr Glu Ala Trp Asp Asp Ile Lys Leu
                85                  90                  95

Cys Phe Pro Asp Cys Tyr Asn Gly Ser Arg Ile Leu Leu Thr Thr Arg
            100                 105                 110

Asn Val Glu Val Ala Glu Tyr Ala Ser Ser Gly Lys Pro Pro His His
        115                 120                 125

Met Arg Leu Met Asn Phe Asp Glu Ser Trp Asn Leu Leu His Lys Lys
    130                 135                 140

Ile Phe Glu Lys Glu Gly Ser Tyr Ser Pro Glu Phe Glu Asn Ile Gly
145                 150                 155                 160

Lys Gln Ile Ala Leu Lys Cys Gly Gly Leu Pro Leu Ala Ile Thr Val
                165                 170                 175

Ile Ala Gly Leu Leu Ser Lys Met Gly Gln Arg Leu Asp Glu Trp Gln
            180                 185                 190

Arg Ile Gly Glu Asn Val Ser Ser Val Ser Thr Asp Pro Glu Ala
        195                 200                 205

Gln Cys Trp Arg Val Leu Ala Leu Ser Tyr His His Leu Pro Ser His
```

```
                    210                 215                 220
Leu Lys Pro Cys Phe Leu Tyr Phe
225                 230

<210> SEQ ID NO 7
<211> LENGTH: 250
<212> TYPE: PRT
<213> ORGANISM: Lycopersicon var.

<400> SEQUENCE: 7

Asn Leu Ala Val Val Pro Ile Val Gly Met Gly Gly Met Gly Lys Thr
  1               5                  10                  15

Thr Leu Ala Lys Ala Val Tyr Asn Asp Glu Arg Val Gln Lys His Phe
                 20                  25                  30

Gly Leu Thr Ala Trp Phe Cys Val Ser Glu Ala Tyr Asp Ala Phe Arg
             35                  40                  45

Leu Thr Lys Gly Ile Leu Gln Glu Ile Gly Ser Thr Asp Leu Lys Ala
 50                  55                  60

Asp Asp Asn Leu Asn Gln Leu Gln Val Lys Leu Lys Ala Asp Asp Asn
 65                  70                  75                  80

Leu Asn Gln Leu Gln Val Lys Leu Lys Glu Lys Leu Asn Gly Lys Arg
                 85                  90                  95

Phe Leu Val Val Leu Asp Asp Val Trp Asn Asp Asn Tyr Pro Glu Trp
            100                 105                 110

Asp Asp Ile Arg Asn Leu Phe Leu Gln Gly Asp Ile Gly Ser Lys Ile
            115                 120                 125

Ile Val Thr Thr Arg Lys Glu Ser Val Ala Leu Met Met Asp Ser Gly
130                 135                 140

Ala Ile Tyr Trp Gly Ile Leu Ser Ser Glu Asp Ser Trp Ala Leu Phe
145                 150                 155                 160

Lys Arg His Ser Leu Glu His Lys Asp Pro Lys Glu His Pro Glu Phe
                165                 170                 175

Glu Glu Val Gly Lys Gln Ile Ala Asp Lys Cys Lys Gly Leu Pro Leu
            180                 185                 190

Ala Leu Lys Ala Leu Ala Gly Met Leu Arg Ser Lys Ser Glu Val Asp
        195                 200                 205

Glu Trp Arg Asn Ile Leu Arg Ser Glu Ile Trp Glu Leu Pro Ser Cys
210                 215                 220

Ser Asn Gly Ile Leu Pro Ala Ile Met Leu Ser Tyr Asn Asp Leu Pro
225                 230                 235                 240

Ala His Leu Lys Gln Cys Phe Ala Tyr Cys
                245                 250

<210> SEQ ID NO 8
<211> LENGTH: 234
<212> TYPE: PRT
<213> ORGANISM: Lycopersicon var.

<400> SEQUENCE: 8

Asn Leu Thr Val Val Pro Ile Val Gly Met Gly Gly Leu Gly Lys Thr
  1               5                  10                  15

Thr Leu Ala Lys Ala Val Tyr Asn Asp Glu Ser Val Lys Asn His Phe
                 20                  25                  30

Asp Leu Lys Ala Trp Phe Cys Val Ser Glu Ala Tyr Asn Ala Phe Arg
             35                  40                  45

Ile Thr Lys Gly Ile Leu Gln Glu Ile Gly Ser Ile Asp Leu Val Asp
```

-continued

```
            50                  55                  60
Asp Asn Leu Asn Gln Leu Gln Val Lys Leu Lys Glu Arg Leu Lys Glu
 65                  70                  75                  80

Lys Lys Phe Leu Ile Val Leu Asp Asp Val Trp Asn Asp Asn Tyr Asn
                 85                  90                  95

Glu Trp Asp Glu Leu Arg Asn Val Phe Val Gln Gly Asp Ile Gly Ser
             100                 105                 110

Lys Ile Ile Val Thr Thr Arg Lys Asp Ser Val Ala Leu Met Met Gly
             115                 120                 125

Asn Glu Gln Ile Ser Met Gly Asn Leu Ser Thr Glu Ala Ser Trp Ser
130                 135                 140

Leu Phe Gln Arg His Ala Phe Glu Asn Met Asp Pro Met Gly His Ser
145                 150                 155                 160

Glu Leu Glu Glu Val Gly Arg Gln Ile Ala Ala Lys Cys Lys Gly Leu
                165                 170                 175

Pro Leu Ala Leu Lys Thr Leu Ala Gly Met Leu Arg Ser Lys Ser Glu
                180                 185                 190

Val Glu Glu Trp Lys Cys Ile Leu Arg Ser Glu Ile Trp Glu Leu Arg
            195                 200                 205

Asp Asn Asp Ile Leu Pro Ala Ile Met Leu Ser Tyr Asn Asp Leu Pro
210                 215                 220

Ala His Leu Phe Arg Cys Phe Ser Phe Cys
225                 230

<210> SEQ ID NO 9
<211> LENGTH: 247
<212> TYPE: PRT
<213> ORGANISM: Arabidopsis sp.

<400> SEQUENCE: 9

Gln Arg Ile Val Val Ala Val Gly Met Gly Ser Gly Lys Thr
  1               5                  10                  15

Thr Leu Ser Ala Asn Ile Phe Lys Ser Gln Ser Val Arg Arg His Phe
             20                  25                  30

Glu Ser Tyr Ala Trp Val Thr Ile Ser Lys Ser Tyr Val Ile Glu Asp
         35                  40                  45

Leu Phe Arg Thr Tyr Ile Lys Glu Phe Tyr Lys Glu Ala Asp Thr Gln
     50                  55                  60

Ile Pro Ala Glu Leu Tyr Ser Leu Gly Tyr Arg Glu Leu Val Glu Lys
 65                  70                  75                  80

Leu Val Glu Tyr Leu Gln Ser Lys Arg Tyr Ile Val Val Leu Asp Asp
                 85                  90                  95

Val Trp Thr Thr Gly Leu Trp Arg Glu Ile Ser Ile Ala Leu Pro Asp
            100                 105                 110

Gly Ile Tyr Gly Ser Arg Val Met Met Thr Thr Arg Asp Met Asn Val
            115                 120                 125

Ala Ser Phe Pro Tyr Gly Ile Gly Ser Thr Lys His Glu Ile Glu Leu
130                 135                 140

Leu Lys Glu Asp Glu Ala Trp Val Leu Phe Ser Asn Lys Ala Phe Pro
145                 150                 155                 160

Ala Ser Leu Glu Gln Cys Arg Thr Gln Asn Leu Glu Pro Ile Ala Arg
                165                 170                 175

Lys Leu Val Glu Arg Cys Gln Gly Leu Pro Leu Ala Ile Ala Ser Leu
                180                 185                 190
```

```
Gly Ser Met Met Ser Thr Lys Lys Phe Glu Ser Glu Trp Lys Lys Val
            195                 200                 205

Tyr Ser Thr Leu Asn Trp Glu Leu Asn Asn His Glu Leu Lys Ile
    210                 215                 220

Val Arg Ser Ile Met Phe Leu Ser Phe Asn Asp Leu Pro Tyr Pro Leu
225                 230                 235                 240

Lys Arg Cys Lys Leu Tyr Cys
                245

<210> SEQ ID NO 10
<211> LENGTH: 331
<212> TYPE: PRT
<213> ORGANISM: Lycopersicon var.

<400> SEQUENCE: 10

His Gln His Leu Arg Ser Leu Ile Thr Thr Asn Arg Ala Lys Ser Ile
1               5                   10                  15

Asn Asp Ile Phe Ser Cys Gln Ile Ser Glu Leu Arg Leu Leu Lys Val
            20                  25                  30

Leu Asp Leu Ser Ser Tyr Ile Val Glu Phe Leu Ser Leu Ala Thr Phe
        35                  40                  45

Lys Pro Leu Asn Gln Leu Lys Tyr Leu Ala Val Gln Ala Phe Glu Phe
    50                  55                  60

Tyr Phe Asp Pro Gly Ser His Leu Pro His Ile Glu Thr Phe Ile Val
65                  70                  75                  80

Met Asn Leu Pro Tyr Tyr Asp Ile Leu Leu Pro Val Ser Phe Trp Glu
                85                  90                  95

Met Lys Lys Leu Arg His Ala His Phe Gly Lys Ala Glu Phe Asp Lys
            100                 105                 110

Gln Gly Leu Ser Glu Gly Ser Ser Lys Leu Glu Asn Leu Arg Ile Leu
        115                 120                 125

Lys Asn Ile Val Gly Phe Asp Arg Val Asp Val Leu Ser Arg Arg Cys
130                 135                 140

Pro Asn Leu Gln Gln Leu Gln Ile Thr Tyr Phe Gly Asn Asn Glu Glu
145                 150                 155                 160

Pro Phe Cys Pro Lys Leu Glu Asn Leu Thr Gln Leu Gln Gln Leu Gln
                165                 170                 175

Leu Pro Phe Ala Arg Pro Arg Thr Leu Ser Gly Leu Gln Leu Pro Ser
            180                 185                 190

Asn Leu Asn Lys Leu Val Leu Glu Gly Ile His Ile Gly Cys Val Ile
        195                 200                 205

Pro Phe Ile Ala Gly Leu Pro Ser Leu Glu Tyr Leu Gln Leu His Asp
    210                 215                 220

Val Cys Phe Pro Gln Ser Glu Glu Trp Cys Leu Gly Asp Ile Thr Phe
225                 230                 235                 240

His Lys Leu Lys Leu Leu Lys Leu Val Lys Leu Asn Ile Ser Arg Trp
                245                 250                 255

Asp Val Ser Glu Glu Ser Phe Pro Leu Leu Glu Thr Leu Val Ile Lys
            260                 265                 270

Lys Cys Ile Asp Leu Glu Glu Ile Pro Leu Ser Phe Ala Asp Ile Pro
        275                 280                 285

Thr Leu Glu Gln Ile Lys Leu Ile Gly Ser Trp Lys Val Ser Leu Glu
    290                 295                 300

Asp Ser Ala Val Arg Met Lys Glu Ile Lys Asp Thr Glu Gly Cys
305                 310                 315                 320
```

```
Asp Arg Leu His Leu Val Lys Gln Arg Ser Asp
            325                 330
```

<210> SEQ ID NO 11
<211> LENGTH: 358
<212> TYPE: PRT
<213> ORGANISM: Lycopersicon var.

<400> SEQUENCE: 11

```
Gly Lys His Leu Tyr Ser Leu Arg Ile Asn Gly Asp Gln Leu Asp Asp
 1               5                  10                  15

Ser Val Ser Asp Ala Phe His Leu Arg His Leu Arg Leu Ile Arg Val
            20                  25                  30

Leu Asp Leu Glu Pro Ser Leu Ile Met Val Asn Asp Ser Leu Leu Asn
        35                  40                  45

Glu Ile Cys Met Leu Asn His Leu Arg Tyr Leu Arg Ile Arg Thr Gln
     50                  55                  60

Val Lys Tyr Leu Pro Phe Ser Phe Ser Asn Leu Trp Asn Leu Glu Ser
 65                  70                  75                  80

Leu Phe Val Ser Asn Lys Gly Ser Ile Leu Val Leu Leu Pro Arg Ile
                85                  90                  95

Leu Asp Leu Val Lys Leu Arg Val Leu Ser Val Gly Ala Cys Ser Phe
            100                 105                 110

Phe Asp Met Asp Ala Asp Glu Ser Ile Leu Ile Ala Lys Asp Ile Lys
        115                 120                 125

Leu Glu Asn Leu Arg Ile Leu Gly Glu Leu Leu Ile Ser Tyr Ser Arg
    130                 135                 140

Asp Thr Met Asn Ile Phe Lys Pro Phe Pro Asn Leu Gln Val Leu Gln
145                 150                 155                 160

Phe Glu Leu Lys Glu Ser Trp Asp Tyr Ser Thr Glu Gln His Trp Phe
                165                 170                 175

Pro Lys Leu Asp Cys Leu Thr Glu Leu Glu Thr Leu Cys Val Gly Phe
            180                 185                 190

Lys Ser Ser Asn Thr Asn His Cys Gly Ser Ser Val Val Thr Asn Arg
        195                 200                 205

Pro Trp Asp Phe His Phe Pro Ser Asn Leu Lys Glu Leu Leu Leu Tyr
    210                 215                 220

Asp Phe Pro Leu Thr Ser Asp Ser Leu Ser Thr Ile Ala Arg Leu Pro
225                 230                 235                 240

Asn Leu Glu Asn Leu Ser Leu Tyr Asp Thr Ile Ile Gln Gly Glu Glu
                245                 250                 255

Trp Asn Met Gly Glu Glu Asp Thr Phe Glu Asn Leu Lys Phe Leu Asn
            260                 265                 270

Leu Arg Leu Leu Thr Leu Ser Lys Trp Glu Val Gly Glu Glu Ser Phe
        275                 280                 285

Pro Asn Leu Glu Lys Leu Lys Leu Gln Glu Cys Gly Lys Leu Glu Glu
    290                 295                 300

Ile Pro Pro Ser Phe Gly Asp Ile Tyr Ser Leu Lys Phe Ile Lys Ile
305                 310                 315                 320

Val Lys Ser Pro Gln Leu Glu Asp Ser Ala Leu Lys Ile Lys Lys Tyr
                325                 330                 335

Ala Glu Asp Met Arg Gly Gly Asn Asp Leu Gln Ile Leu Gly Gln Arg
            340                 345                 350

Asn Ile Pro Leu Phe Lys
```

<210> SEQ ID NO 12
<211> LENGTH: 355
<212> TYPE: PRT
<213> ORGANISM: Lycopersicon var.

<400> SEQUENCE: 12

Val Arg Ser Leu Leu Phe Asn Ala Ile Asp Pro Asp Asn Leu Leu Trp
 1               5                  10                  15

Pro Arg Asp Ile Ser Phe Ile Phe Glu Ser Phe Lys Leu Val Lys Val
             20                  25                  30

Leu Asp Leu Glu Ser Phe Asn Ile Gly Gly Thr Phe Pro Thr Glu Ile
         35                  40                  45

Gln Tyr Leu Ile Gln Met Lys Tyr Phe Ala Ala Gln Thr Asp Ala Asn
     50                  55                  60

Ser Ile Pro Ser Ser Ile Ala Lys Leu Glu Asn Leu Glu Thr Phe Val
 65                  70                  75                  80

Val Arg Gly Leu Gly Gly Glu Met Ile Leu Pro Cys Ser Leu Leu Lys
                 85                  90                  95

Met Val Lys Leu Arg His Ile His Val Asn Asp Arg Val Ser Phe Gly
            100                 105                 110

Leu His Glu Asn Met Asp Val Leu Thr Gly Asn Ser Gln Leu Pro Asn
        115                 120                 125

Leu Glu Thr Phe Ser Thr Pro Arg Leu Phe Tyr Gly Arg Asp Ala Glu
    130                 135                 140

Lys Val Leu Arg Arg Met Pro Lys Leu Arg Lys Leu Ser Cys Ile Phe
145                 150                 155                 160

Ser Gly Thr Phe Gly Tyr Ser Arg Lys Leu Lys Gly Arg Cys Val Arg
                165                 170                 175

Phe Pro Arg Leu Asp Phe Leu Ser His Leu Glu Ser Leu Lys Leu Val
            180                 185                 190

Ser Asn Ser Tyr Pro Ala Lys Leu Pro His Lys Phe Asn Phe Pro Ser
        195                 200                 205

Gln Leu Arg Glu Leu Thr Leu Ser Lys Phe Arg Ile Pro Trp Thr Gln
    210                 215                 220

Ile Ser Ile Ile Ala Glu Leu Pro Asn Leu Val Ile Leu Lys Leu Leu
225                 230                 235                 240

Leu Arg Ala Phe Gln Gly Asp His Trp Glu Val Lys Asp Ser Glu Phe
                245                 250                 255

Leu Glu Leu Lys Tyr Leu Lys Leu Asp Asn Leu Lys Val Val Gln Trp
            260                 265                 270

Ser Ile Ser Asp Asp Ala Phe Pro Lys Leu Glu His Leu Val Leu Thr
        275                 280                 285

Lys Cys Lys His Leu Glu Lys Ile Pro Ser Arg Phe Glu Asp Ala Val
    290                 295                 300

Cys Leu Asn Arg Val Glu Val Asn Trp Cys Asn Trp Asn Val Ala Asn
305                 310                 315                 320

Ser Ala Gln Asp Ile Gln Thr Met Gln His Glu Val Ile Ala Asn Asp
                325                 330                 335

Ser Phe Thr Val Thr Ile Gln Pro Pro Asp Trp Ser Arg Glu Gln Pro
            340                 345                 350

Leu Asp Ser
        355